United States Patent
Park et al.

(10) Patent No.: US 9,734,602 B2
(45) Date of Patent: Aug. 15, 2017

(54) IMAGE PROCESSING APPARATUS AND METHOD FOR CONTROLLING THE SAME

(71) Applicant: SAMSUNG ELECTRONICS CO., LTD., Suwon-si (KR)

(72) Inventors: Sungchan Park, Suwon-si (KR); Jooyoung Kang, Yongin-si (KR); Jungho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 82 days.

(21) Appl. No.: 14/801,415

(22) Filed: Jul. 16, 2015

(65) Prior Publication Data

US 2016/0019702 A1  Jan. 21, 2016

(30) Foreign Application Priority Data

Jul. 16, 2014 (KR) .................. 10-2014-0089475

(51) Int. Cl.

| G06T 11/00 | (2006.01) |
|---|---|
| G06T 11/60 | (2006.01) |
| G06T 7/00 | (2017.01) |
| G01S 15/89 | (2006.01) |
| G01S 7/52 | (2006.01) |
| A61B 8/00 | (2006.01) |
| A61B 8/08 | (2006.01) |

(52) U.S. Cl.
CPC ........ *G06T 11/008* (2013.01); *G01S 7/52038* (2013.01); *G01S 7/52047* (2013.01); *G01S 15/8977* (2013.01); *G06T 11/60* (2013.01); *A61B 8/4405* (2013.01); *A61B 8/5207* (2013.01); *G01S 15/8915* (2013.01)

(58) Field of Classification Search
CPC .... G06T 11/008; G06T 11/60; G01S 15/8977; G01S 7/52047; G01S 7/52038; G01S 15/8915; A61B 8/5207; A61B 8/4405
See application file for complete search history.

(56) References Cited

U.S. PATENT DOCUMENTS

| 2002/0009204 A1* | 1/2002 | Matsumura | ......... G01S 7/52038 |
|---|---|---|---|
| | | | 381/98 |
| 2014/0185759 A1* | 7/2014 | Kang | .................... G01N 23/04 |
| | | | 378/62 |

OTHER PUBLICATIONS

Taxt et al. "Superresolution of Ultrasound Images Using the First and Second Harmonic Signal." IEEE Transactions on Ultasonics, Ferroelectrics, and Frequency Control, vol. 51, No. 2, Feb. 2004, pp. 163-175.*

Michailovich et al. "A Novel Approach to the 2-D Blind Deconvolution Problem in Medical Ultrasound." IEEE Transactions on Medical Imaging, vol. 24, No. 1, Jan. 2005, pp. 86-104.*

* cited by examiner

*Primary Examiner* — Jon Chang
(74) *Attorney, Agent, or Firm* — Sughrue Mion, PLLC

(57) ABSTRACT

An apparatus for processing a medical image includes: a receiver configured to receive a signal having a plurality of frequency bands; an image reconstructor configured to segment the signal into a first signal of a first frequency band and a second signal of a second frequency band based on a signal strength, and configured to generate a first reconstructed image of the first frequency band and a second reconstructed image of the second frequency band; and an image synthesizer configured to synthesize the first reconstructed image and the second reconstructed image.

22 Claims, 24 Drawing Sheets

IMAGE PROCESSING APPARATUS AND METHOD FOR CONTROLLING THE SAME

CROSS-REFERENCE TO RELATED APPLICATION(S)

This application claims priority from Korean Patent Application No. 10-2014-0089475, filed on Jul. 16, 2014 in the Korean Intellectual Property Office, the disclosure of which is incorporated herein by reference in its entirety.

BACKGROUND

1. Field

Apparatuses and methods consistent with exemplary embodiments relate to image processing in a medical imaging apparatus.

2. Description of the Related Art

An image processing apparatus (e.g., a medical imaging apparatus) is an apparatus which acquires information of a patient and provides an image of the acquired information. For example, the image processing apparatus includes an X-ray imaging apparatus, an ultrasonic diagnostic apparatus, a computed tomography (CT) scanner, a magnetic resonance imaging (MRI) apparatus, and the like.

The above image processing apparatuses have respective characteristics. For example, the magnetic resonance imaging (MRI) device does not have radiation exposure, and provides a relatively free imaging condition, high contrast in soft tissue, and a variety of diagnostic information images. However, the MRI device has a relatively longer image acquisition time and a higher cost. Also, an ultrasound diagnostic apparatus does not provide a relatively high resolution.

SUMMARY

One or more exemplary embodiments provide an image processing apparatus for performing image segmentation and image synthesis according to a plurality of frequency bands to perform image processing on a medical image.

In accordance with an aspect of an exemplary embodiment, an image processing apparatus includes: a receiver to receive a signal having a plurality of frequency bands; an image reconstructor to segment the signal into a signal of a first frequency band and a signal of a second frequency band in a manner that the second frequency band signal includes a signal strength of more than a threshold value, and to form a first reconstructed image of the first frequency band and a second reconstructed image of the second frequency band; and an image synthesizer to synthesize the first reconstructed image and the second reconstructed image.

The image reconstructor may segment the signal in a manner that the first frequency band and the second frequency band include uniform signal strength.

The image reconstructor may segment the signal into a signal of a fundamental band and a signal of a harmonic band in such a manner that the harmonic band signal includes a signal-to-noise ratio (SNR) having a threshold value or higher. The image reconstructor may form a reconstructed image of the fundamental band and a reconstructed image of the harmonic band.

The image reconstructor may gradually extend a bandwidth of the harmonic band as the signal is located closer to a focusing-point region.

The image reconstructor may perform a deconvolution between the respective segmented signals.

The image reconstructor may estimate a point spread function (PSF) of each segmented signal, and may perform a deconvolution between each segmented signal and the point spread function (PSF), resulting in formation of a reconstructed image.

The image reconstructor may include: an image segmentor to segment the signal into a signal of a first frequency band and a signal of a second frequency band in such a manner that the second frequency band signal includes a signal strength of more than a threshold value; a point spread function (PSF) estimator to estimate a point spread function (PSF) of each segmented signal; and a deconvolution unit to generate a first reconstructed image and a second reconstructed image by performing a deconvolution between a point spread function (PSF) corresponding to each of the segmented signals and each segmented signal.

The image synthesizer may allocate different weights to a first reconstructed image and a second reconstructed image according to a contrast-to-noise ratio (CNR) of a region of interest, and may synthesize the first reconstructed image and the second reconstructed image.

The image synthesizer may allocate a weight proportional to contrast strength of a region of interest to the second reconstructed image, and may synthesize the first reconstructed image and the second reconstructed image.

The image synthesizer may form a combination image by synthesizing the first reconstructed image and the second reconstructed image, and may divide the combination image into two regions through binary coding of the combination image. In case of one of the two regions, different weights may be assigned to the first reconstructed image and the second reconstructed image according to a contrast-to-noise ratio (CNR) strength of a region of interest. In case of the other one of the two regions, the same weight may be assigned to the first reconstructed image and the second reconstructed image.

The image synthesizer may include: an image combiner to form a combination image by combining the first reconstructed image and the second reconstructed image; a binary image generator to perform binary coding of the combination image according to brightness; a contrast-to-noise ratio (CNR) to calculate a CNR of a region of interest; and a weight applier to assign different weights to the first reconstructed image and the second reconstructed image according to the CNR of the interest region.

The image combiner may combine the first reconstructed image and the second reconstructed image to which different weights are assigned.

In accordance with an aspect of an exemplary embodiment, a method for controlling an image processing apparatus includes: receiving a signal having a plurality of frequency bands; segmenting the signal into a signal of a first frequency band and a signal of a second frequency band in a manner that the second frequency band signal includes a signal strength of more than a threshold value; forming a first reconstructed image of the first frequency band and a second reconstructed image of the second frequency band; and synthesizing the first reconstructed image and the second reconstructed image.

The segmentation operation may include: performing signal segmentation in a manner that the first frequency band and the second frequency band have uniform signal strength.

The segmentation operation may include segmenting the signal into a signal of a fundamental frequency band and a signal of a harmonic frequency band in such a manner that the harmonic frequency band signal includes a signal-to-noise ratio (SNR) having a threshold value or higher. The forming operation of the reconstructed images may include forming a reconstructed image of the fundamental frequency band and a reconstructed image of the harmonic frequency band.

The segmentation operation may gradually extend a bandwidth of the harmonic band as the signal is located closer to a focusing-point region.

The formation operation may perform a deconvolution between the respective segmented signals.

The synthesizing operation may include assigning different weights to the first reconstructed image and the second reconstructed image according to contrast strength of a region of interest, so that the first reconstructed image and the second reconstructed image are synthesized.

The synthesizing operation may include allocating a weight proportional to contrast strength of a region of interest to the second reconstructed image, so that the first reconstructed image and the second reconstructed image are synthesized.

The synthesizing operation may include: forming a combination image by synthesizing the first reconstructed image and the second reconstructed image; and dividing the combination image into two regions through binary coding of the combination image, wherein, in case of one of the two regions, the same weight is assigned to the first reconstructed image and the second reconstructed image, and in case of the other one of the two regions, different weights are assigned to the first reconstructed image and the second reconstructed image according to a contrast strength of the interest region.

BRIEF DESCRIPTION OF THE DRAWINGS

The above and/or other aspects will become more apparent by describing certain exemplary embodiments with reference to the accompanying drawings.

DETAILED DESCRIPTION

Figure 1:
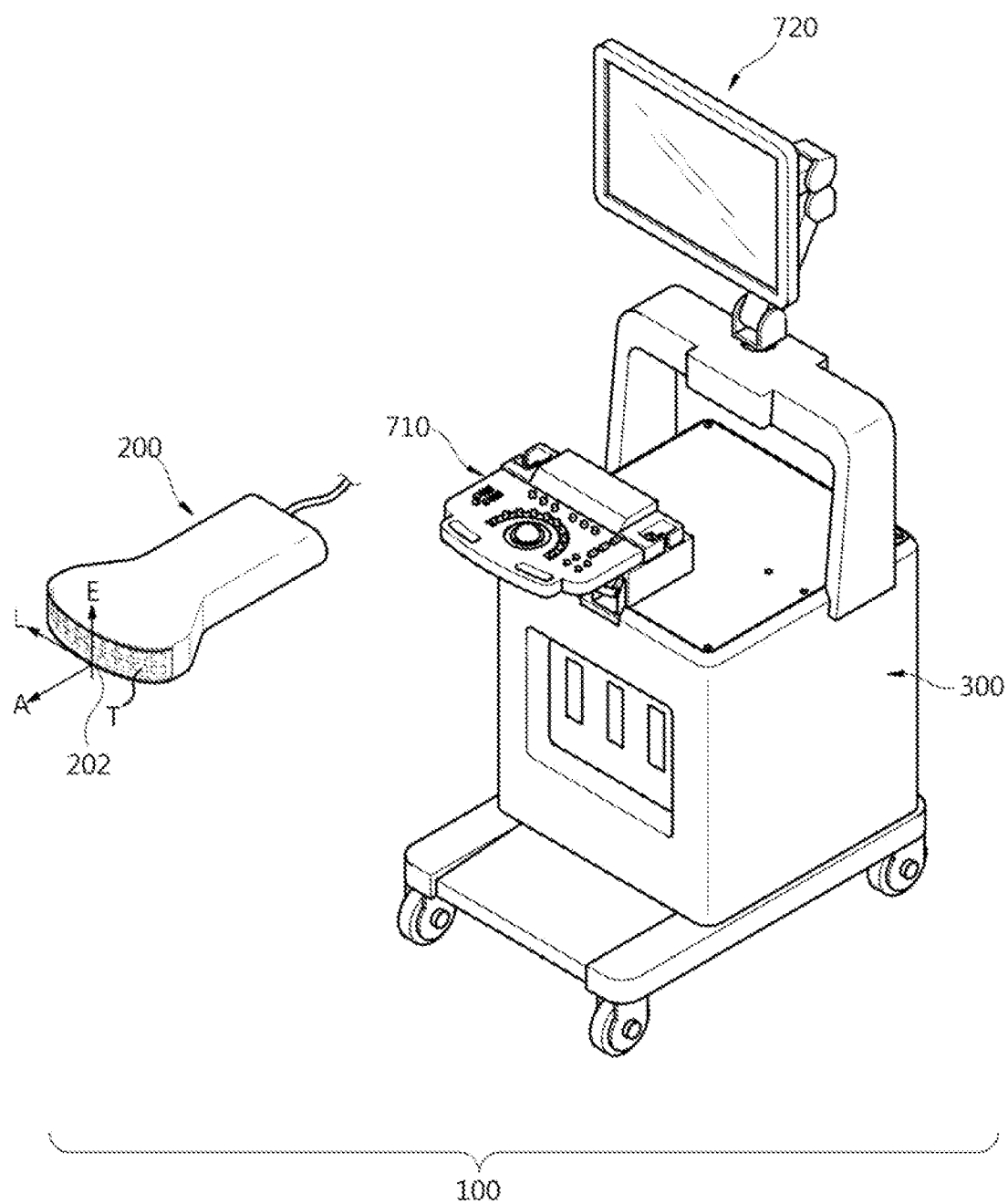
FIG. 1 is a perspective view illustrating an ultrasonic imaging apparatus according to an exemplary embodiment.

Reference will now be made in detail to exemplary embodiments with reference to the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the present description.

In the following description, descriptions of known functions or structures, which may obscure the subject matter of the exemplary embodiments, may be omitted. It will be understood that, although the terms first, second, etc. may be used herein to describe various elements, components, regions, and/or sections, these elements, components, regions, layers and/or sections should not be limited by these terms. An image processing apparatus according to the exemplary embodiments may include an image capture part (also called an image photographing part) for capturing (or photographing) images of an internal or external region of an object, and a host device for registering images received from the image capture part.

The image capture part may be spaced apart from the host device of the image processing apparatus by a predetermined distance. The image capture part may be connected to the host device through various wired and/or wireless communication protocols, or may be coupled to one device.

For example, the image capture part may communicate with the host device according to the digital imaging and communications in medicine (DICOM) standard. For example, although the image capture part can communicate using the DICOM standard, the exemplary embodiments are not limited thereto. The image capture part may be connected to the host device through a mobile communication protocol (e.g., global system for mobile communication (GSM), code division multiple access (CDMA), wideband code division multiple access (WCDMA), time division multiple access (TDMA), long term evolution (LTE)) or a near field communication protocol (e.g., wireless local access network (WLAN), Bluetooth, Zigbee, and near field communication (NFC)).

In this case, the image capture part may obtain an image (hereinafter referred to as an internal image) regarding an internal structure of an object. That is, the image capture part may obtain an internal image using radiation, a magnetic resonance phenomenon, or ultrasonic waves. For example, the image capture part may obtain an internal image of an object using a radiation based method such as computed tomography (CT), positron emission tomography (PET), single photon emission computed tomography (SPECT), or mammography, or may obtain an internal image of an object using ultrasonic waves.

As described above, although the image capture part can obtain images of the object using various image acquisition methods, the respective image acquisition methods have merits and demerits. For example, the computed tomography (CT) apparatus has a relatively short image acquisition time and costs less, and the magnetic resonance imaging (MRI) apparatus has a relatively long image acquisition time and a high cost. However, the MRI apparatus has an advantage in that the MRI apparatus can obtain a higher-resolution image than the CT apparatus.

In addition, the respective image acquisition methods have different preferences according to internal structures or characteristics of an object. For example, if the object is a human body, different image acquisition methods may be applied to respective internal organs of the human body according to structures or characteristics of the internal organs. Therefore, an image of a target site of the human body is acquired by a preferred image acquisition method for each internal organ, and images acquired by the preferred image acquisition methods of respective internal organs are registered so that a disease can be more easily diagnosed. In addition, images can be obtained by the preferred methods of the respective internal organs, resulting in reduction of time and costs consumed to acquire images needed for diagnosis.

For convenience of description, although the ultrasonic imaging apparatus for acquiring images using the ultrasonic imaging scheme will hereinafter be described as an example of the image processing apparatus, the exemplary embodiments are not limited thereto, and the above image capturing scheme may be replaced by other methods for acquiring internal images of the object. In addition, many more image acquisition methods can also be applied to the exemplary embodiments so that desired images can be obtained.

The ultrasonic imaging apparatus and a method for controlling the same according to the exemplary embodiments will hereinafter be described with reference to the drawings.

FIG. 1 is a perspective view illustrating an ultrasonic imaging apparatus according to an exemplary embodiment.

Referring to FIG. 1, an ultrasonic imaging apparatus 100 according to an exemplary embodiment may include a probe 200, a main body 300, an input unit 710, and a display 720.

One end of a cable may be connected to the probe 200, and a male connector (not shown) may be connected to the other end of the cable. The male connector connected to the other end of the cable may be physically coupled to a female connector of the main body 300.

The probe 200 includes at least one transducer T, transmits ultrasonic waves to an object using the transducer T, and receives echo ultrasonic waves from the object. At least one transducer T may form at least one column, and may be provided at one end of the probe 200, as shown in FIG. 1.

Although the object may be a living body of a human or an animal, and a target site of the object may be a tissue in the living body, such as blood vessels, bones, muscles, or the like, the exemplary embodiments are not limited thereto, and all kinds of objects, internal structures of which can be imaged, may be used.

Three directions perpendicular to one another with respect to a center point 202 of the transducer T may be defined as an axis direction (A), a lateral direction (L), and an elevation direction (E). In more detail, a direction of ultrasonic transmission is defined as the axis direction (A), a direction along which a column of the transducer T is arranged is defined as the lateral direction (L), and a direction perpendicular to the (A) and (L) directions may be defined as the elevation direction (E).

The main body 300 may include main elements of the ultrasonic imaging apparatus 100. For example, the main body 300 may include a transmit (Tx) signal generator (See 361 of FIG. 3).

If a user or an inspector inputs an ultrasonic diagnosis command, the transmit (Tx) signal generator 361 generates a transmit (Tx) signal, and transmits the transmit (Tx) signal to the probe 200.

One or more female connectors (not shown) may be contained in the main body 300 and coupled to male connectors (not shown) that are coupled to the cable, such that the main body 300 can communicate with the probe 200. For example, the transmit (Tx) signals generated by the transmit (Tx) signal generator 361 may be applied to the probe 200 through the male connectors coupled to the female connectors of the main body 300 and the cable.

In addition, a plurality of casters (not shown) for moving the ultrasonic imaging apparatus 100 in a specific direction may be provided at a lower part of the main body 300.

The plurality of casters may fix the ultrasonic imaging apparatus 100 in a specific place or allow the ultrasonic imaging apparatus 100 to move in a specific direction.

The input unit 710 may receive commands regarding the operations of the ultrasonic imaging apparatus 100. For example, the input unit 710 may receive commands to select one of ultrasonic diagnosis start, diagnosis part selection, diagnosis category selection, and mode selection of the output ultrasonic images, from the user. The commands inputted through the input unit 710 may be transmitted to the main body 300 through wired communication or wireless communication.

Here, the user may be, but not limited to, a person who diagnoses the object using the ultrasonic imaging apparatus 100, for example, a doctor, radiologist, or nurse, and may include any one who uses the ultrasonic imaging apparatus 100.

The ultrasonic imaging apparatus 100 may acquire an amplitude mode (A-mode) image, a brightness mode (B-mode) image, a Doppler mode (D-mode) image, a motion mode (M-mode) image, an elastography mode (E-mode) image, etc.

The input unit 710 may include at least one of a keyboard, a mouse, a trackball, a touchscreen, a foot switch, and a foot pedal, without being limited thereto.

The input unit 710 may be located at an upper part of the main body 300 as shown in FIG. 1. However, if the input unit 710 is implemented as a foot switch or a foot pedal, the input unit 710 may be provided at the lower part of the main body 300.

If the input unit 710 is implemented as a graphical user interface (GUI) such as a touchscreen, i.e., if the input unit 710 is implemented by software, the input unit 710 may be displayed through a display 720 to be described later.

At least one probe holder may be disposed around the input unit 710. Therefore, a user may place the probe 200 at the probe holder when the ultrasonic imaging apparatus 100 is not used.

The display 720 may display images acquired from the ultrasonic diagnosis process. The display 720 may display images in response to a mode selected by the user. If user selection is not present, images may be displayed in a default mode (e.g., B mode). For example, the default mode may be preset by the user. In addition, the display 720 may also display ultrasonic images to which a predetermined image processing has been applied by an image processor 500, which will be described later.

Although the display 720 may be coupled to the main body 300 as shown in FIG. 1, it should be noted that the display 720 can also be detachably coupled to the main body 300, if needed. Although not shown in FIG. 1, the ultrasonic imaging apparatus 100 may further include an additional sub-display for displaying applications (e.g., menu or information needed for ultrasonic diagnosis) associated with the operations of the ultrasonic imaging apparatus 100, A cathode ray tube (CRT), liquid crystal display (LCD), or light emitting diode (LED) may be used as the display 720. However, the exemplary embodiments are not limited thereto.

Figure 2:
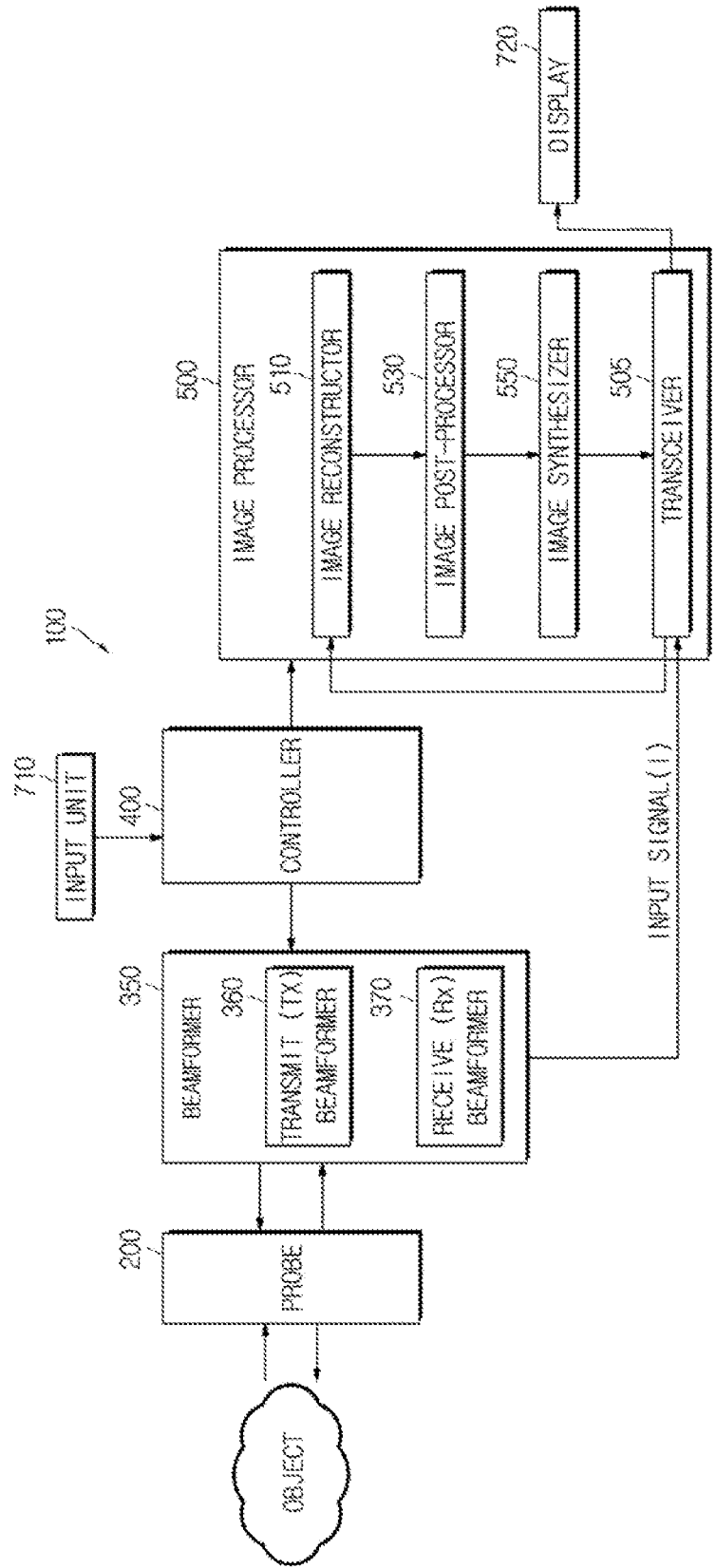
FIG. 2 is a block diagram illustrating an ultrasonic imaging apparatus according to an exemplary embodiment.

FIG. 2 is a block diagram illustrating an ultrasonic imaging apparatus according to an exemplary embodiment.

Referring to FIG. 2, the ultrasonic imaging apparatus 100 includes a probe 200, a beamformer 350, a controller 400, an image processor 500, an input unit 710, and a display 720, such that the ultrasonic imaging apparatus 100 may capture an image of an inside of an object using the above elements.

The controller 400 may provide overall control to the ultrasonic imaging apparatus 100. In more detail, the controller 400 may generate a control signal for controlling at least one of a transmit (Tx) beamformer 360, a receive (Rx) beamformer 370, an image processor 500, and a display 720 in response to instructions or commands input through the input unit 710. When needed, the controller 400 may also generate control signals for controlling respective constituent elements of the ultrasonic imaging apparatus 100 in response to instructions or commands received from an external device through wired or wireless communication. For example, the controller 400 may be a processor.

In addition, the controller 400 may include a read only memory (ROM) and a random access memory (RAM). The ROM may store control programs for controlling the processor and/or the ultrasonic imaging apparatus 100. The RAM may store signals or data received from an external source by the ultrasonic imaging apparatus 100, or may be used as a storage region corresponding to various tasks executed by the ultrasonic imaging apparatus 100.

The processor may be implemented in the form of a System On Chip (SOC) including a core and/or a Graphic Processor (GPU). The processor may include a single core, a dual core, a triple core, a quad core, or any suitable architecture.

The controller 400 may include a graphics processing board including the processor, RAM and/or ROM in a circuit board electrically coupled to the controller 400. The processor, the ROM, and the RAM may be connected to one another through an internal bus.

The probe 200 includes at least one transducer T, transmits ultrasonic waves to the object, and receives echo ultrasonic waves reflected from the object, such that electric signals can be converted into ultrasonic waves and vice versa.

In more detail, if the probe 200 receives a current from an external power source or an internal storage such as a battery, respective transducers are vibrated to generate ultrasonic waves, so that the ultrasonic waves are applied to an external object. The respective transducers are configured to receive echo ultrasonic waves reflected from the object, and are vibrated according to the received echo ultrasonic waves, resulting in creation of a current of a frequency corresponding to a vibration frequency.

Examples of the transducers T may include a magnetostrictive ultrasonic transducer using magnetostrictive effects of a magnetic material, a capacitive micromachined ultrasonic transducer (cMUT) to transmit and receive ultrasonic waves using vibration of several hundred or thousand micromachined thin films, and a piezoelectric ultrasonic transducer using piezoelectric effects of a piezoelectric material. Hereinafter, a piezoelectric ultrasonic transducer will be described as one exemplary embodiment of the transducer.

The transducer T may be any one of a linear-array transducer, a convex-array transducer, a phased-array transducer, a sector-array transducer, etc. In this case, the array form may be shaped in a line or in a matrix form. If the transducers are arranged in a line, the transducers may swing in an elevation direction to acquire a plurality of ultrasonic images. If the transducers are arranged in a matrix form, the transducers can acquire a plurality of ultrasonic images through only one transmission of ultrasonic waves.

In addition, the transducers can generate pulsed ultrasonic waves, without being limited thereto. The transducers may also generate ultrasonic waves using excitation coding such as Golay or Chirp coding. If Chirp coding is used, frequency modulation signals are used so that the ultrasonic imaging apparatus can synthesize or combine broadband frequency signals.

However, the exemplary embodiments are not limited thereto, and the transducers may also be implemented as any other kinds of transducers well known to those skilled in the art.

The beamformer 350 may include the transmit (Tx) beamformer 360 and the receive (Rx) beamformer 370. The beamformer 350 may perform analog-to-digital conversion (ADC) or digital-to-analog conversion (DAC), such that a difference in time between an ultrasonic signal transmitted from at least one transducer T and another ultrasonic signal received from at least one transducer can be adjusted.

The structure and operations of the beamformer 140 will hereinafter be described with reference to FIGS. 3 and 4.

Figure 3:
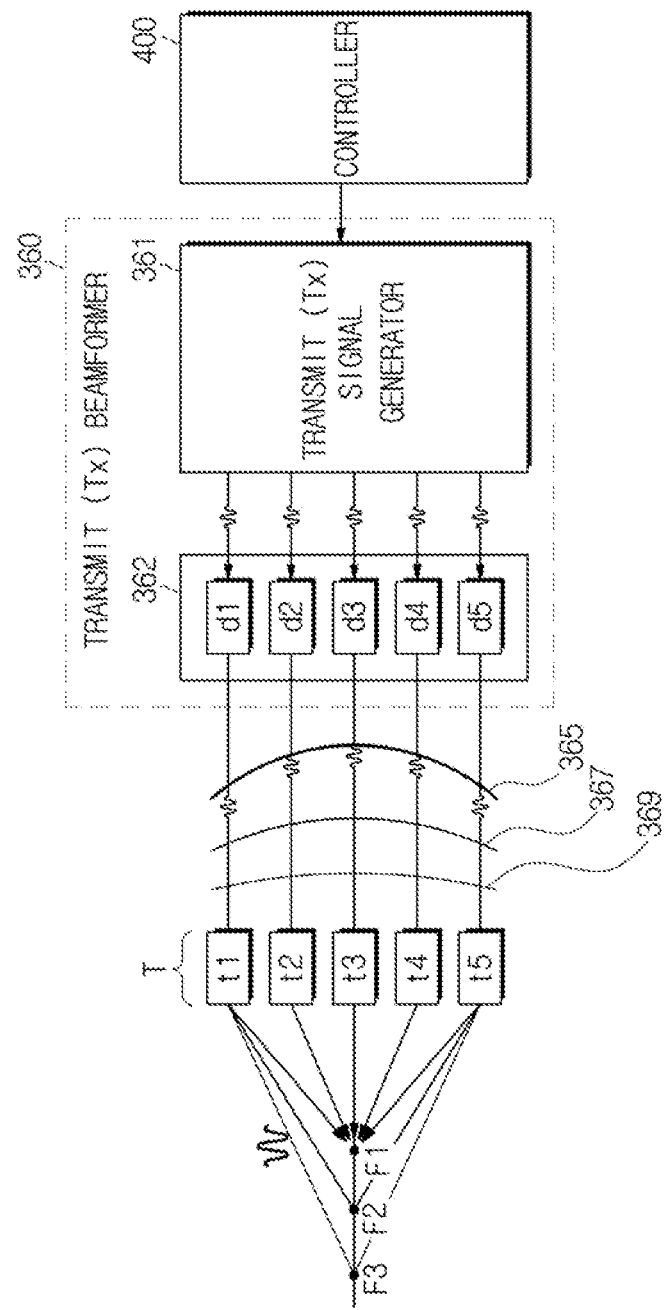
FIG. 3 is a conceptual diagram illustrating a transmission beamformer.

FIG. 3 is a conceptual diagram illustrating a transmit (Tx) beamformer 360. FIG. 4 is a conceptual diagram illustrating a receive (Rx) beamformer 370.

Referring to FIG. 3, the transmission beamformer 360 may perform transmit (Tx) beamforming using a transmit (Tx) signal generator 361 and a time delayer 362. The transmit (Tx) beamforming may be performed such that ultrasonic waves generated from at least one transducer T are focused on a focal point. That is, the transmit (Tx) beamforming may be performed such that an appropriate sequence is determined to overcome a time difference between time points at which ultrasonic waves generated from at least one transducer T arrive at the focal point, and the at least one transducer T generates the ultrasonic waves according to the determined sequence.

In more detail, the transmit (Tx) signal generator 361 of the transmit (Tx) beamformer may output a transmit (Tx) signal to at least one transducer T upon receiving a control signal from the controller 400. In this case, the transmit (Tx) signal may be a high-frequency alternating current (AC) signal, and as many transmit (Tx) signals as the number of transducers may be generated. The transmit (Tx) signal generated from the transmit (Tx) signal generator 361 may be transmitted to the time delayer 362.

The time delayer 362 adds a time delay to each transmit (Tx) signal, so that the time at which the transmit (Tx) signal arrives at the corresponding transducer T can be adjusted.

If the transmit (Tx) signal delayed by the time delayer 362 is applied to the transducer T, the transducer T may generate ultrasonic waves corresponding to the frequency of the transmit (Tx) signal. The ultrasonic waves generated from the respective transducers T are focused on a focal point. The position of the focal point at which ultrasonic waves generated from the transducers T are focused may be changed according to which delay pattern is applied to the transmit (Tx) signal.

The transducer T including five transducers t1, t2, t3, t4, t5 are exemplarily shown in FIG. 3. For example, three delay patterns 365, 367, 369 applicable to the transmit (Tx) signals are denoted by a thick solid line, a medium-thick solid line, and a thin solid line, respectively.

If the delay pattern 365 denoted by the thick solid line is applied to the transmit (Tx) signals generated from the Tx signal generator 361, ultrasonic waves generated from the respective transducers t1~15 are focused on a first focal point F1.

If the delay pattern 367 denoted by the medium-thick solid line is applied to the respective Tx signals generated from the Tx signal generator 361, the ultrasonic waves generated from the respective transducers t1~t5 are focused on a second focal point F2 located further away from the transmit (Tx) beamformer 360 than the first focal point F1.

If the delay pattern 369 denoted by a thin solid line is applied to the respective transmit (Tx) signals generated from the transmit (Tx) signal generator 361, ultrasonic waves generated from the respective transducers t1~t5 are focused on a third focal point F3 located further away from the transmit (Tx) beamformer 360 than the second focal point F2.

As described above, the location of the focal point may be changed according to a delay pattern applied to the transmit (Tx) signal generated from the transmit (Tx) signal generator 361.

If only one delay pattern is applied to the respective transmit (Tx) signals, ultrasonic waves applied to the object are focused on a single focal point. The focusing at only one focal point may be referred to as fixed-focusing. On the other hand, if another delay pattern is applied to the respective transmit (Tx) signals, ultrasonic waves applied to the object are focused at a plurality of focal points. The focusing at multiple focal points may be referred to as multi-focusing.

As described above, the ultrasonic waves generated from the respective transducers T may be focused at only one focal point or at multiple focal points, and the focused ultrasonic waves are applied to the inside of the object. Ultrasonic waves applied to the inside of the object are reflected from a target site within the object, and the reflected echo ultrasonic waves are received by the transducers T. The transducers T may convert the received echo ultrasonic waves into electrical signals, and output the resultant electrical signals. In this case, the converted electrical signals may be defined as receive (Rx) signals. The receive (Rx) signals generated from the transducers T are amplified and filtered, and converted into digital signals, such that the resultant digital signals are provided to the receive (Rx) beamformer 370.

Figure 4:
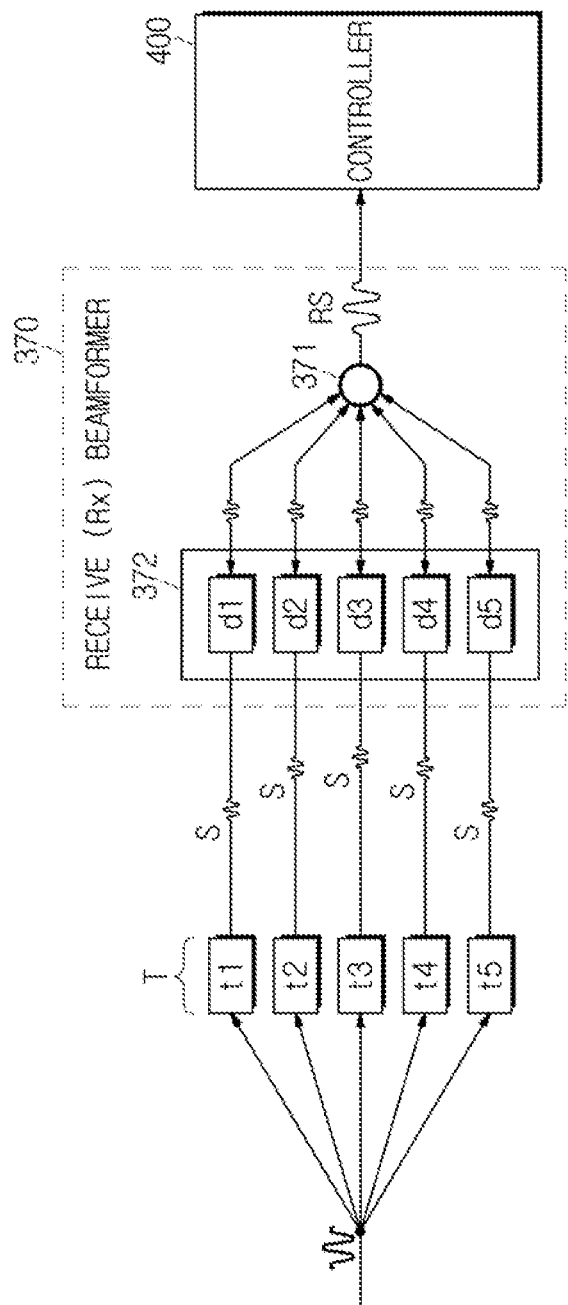
FIG. 4 is a conceptual diagram illustrating a reception beamformer.

Referring to FIG. 4, the receive (Rx) beamformer 370 includes a time-difference corrector 372 and a focuser 371. The receive (Rx) beamformer 370 may perform receive (Rx) beamforming on the receive (Rx) signals (S) denoted by digital signals. The Rx beamforming may be performed such that a time difference among Rx signals (S) generated from the respective transducers T is corrected and the Rx signals (S) are then focused.

In more detail, the Rx signals (S) generated from the respective transducers T are delayed for a predetermined time, so that the resultant Rx signals (S) can be transferred to the focuser 371 at the same time.

The Rx signals (S), a time difference of which is corrected by the time-difference corrector 372, can be focused on a single focal point.

The focuser 371 may add a predetermined weight (e.g., a beamforming coefficient) to each input Rx signal (S), so that a predetermined Rx signal (S) from among a plurality of Rx signals can be emphasized or attenuated than other Rx signals (S) and the resultant Rx signals (S) can be focused. The focused Rx signals (RS) may be provided to the image processor 500. Here, signals applied to the image processor 500 may be defined as input signals (I).

Referring again to FIG. 2, the image processor 500 may include a transceiver 505, an image reconstructor 510, an image post-processor 530, and an image synthesizer 550.

The image processor 500 segments an ultrasonic image into a plurality of ultrasonic images of a plurality of frequency bands using unique characteristics that different signal-to-noise ratios (SNRs) are assigned to the respective frequency bands. Then, the image processor 500 estimates a point spread function (PSF) for each segmented ultrasonic image, and performs deconvolution based on the estimated PSF, such that the image processor 500 may obtain a reconstructed image very similar to a raw image of the target site. In addition, the image processor 500 may combine or synthesize the reconstructed images of the respective frequency bands according to brightness of a region of interest, such that a combined image (i.e., a composite or synthetic image) is generated.

Hereinafter, a more detailed description of a raw image and a reconstructed image will be given with reference to FIGS. 5A, 5B, 6, 7, 8A, and 8B.

Figure 5A:
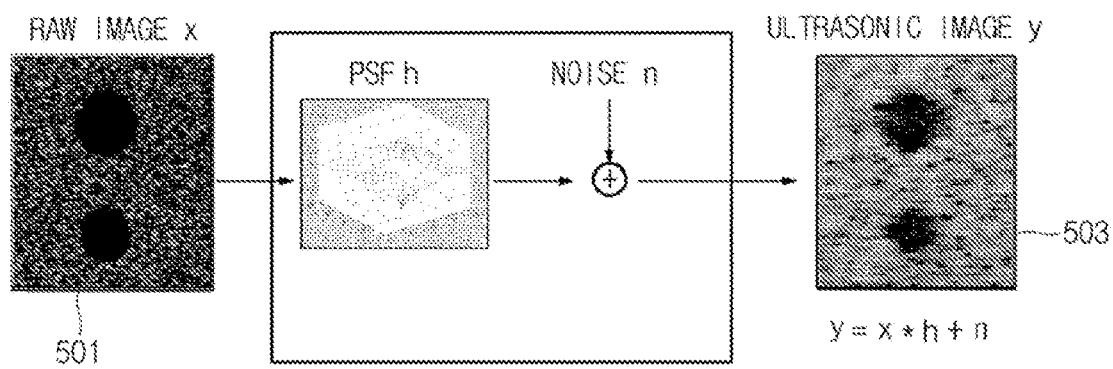
FIG. 5A is a conceptual diagram illustrating a relationship between a raw image of a target site inside an object and an ultrasonic image of the target site and FIG. 5B is a conceptual diagram illustrating a relationship between an ultrasonic image of a target site inside an object and a reconstructed image of the target site.
Figure 5B:
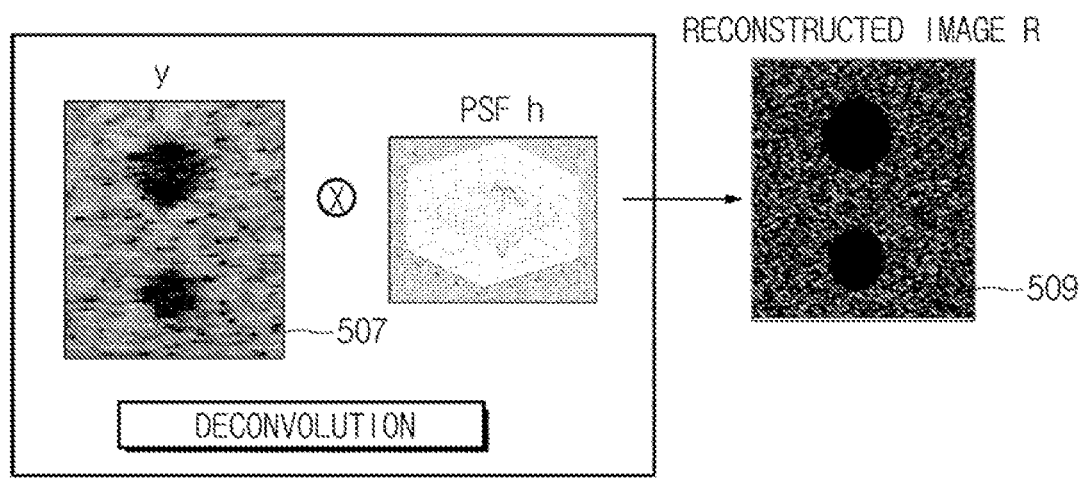

FIG. 5A is a conceptual diagram illustrating a relationship between a raw image of a target site inside the object and an ultrasonic image of the target site. FIG. 5B is a conceptual diagram illustrating a relationship between an ultrasonic image of a target site and a reconstructed image of the target site.

A raw image x 501 and an ultrasonic image y 503 are shown in FIG. 5A. An ultrasonic image y 507 and a reconstructed image R 509 are shown in FIG. 5B. The raw image x 501 is an ideal image of a target site of the object, and the ultrasonic image y 503 is an image generated in response to the above-mentioned input signals (I). The reconstructed image R 509 may be an image obtained when the ultrasonic image y 503 is reconstructed to be approximate to the raw image x 501.

The input signals (I) may be provided after completion of ultrasound transmission and/or reception (Tx and/or Rx) by the probe 200 and beamforming by the beamformer 350. If ultrasonic waves are transmitted to the target point, an intended effect may occur. The term "intended effect" may indicate, for example, formation of two-dimensional (2D) or three-dimensional (3D) image of a target site, thermal deformation of the target site, or destruction of some cells of the target site, but the exemplary embodiments are not limited thereto.

Ultrasonic waves (or incident waves) generated by the probe 200 may be distorted while arriving at the object, such that the input signals (I) corresponding to the reflected waves may include harmonic components.

Figure 6:
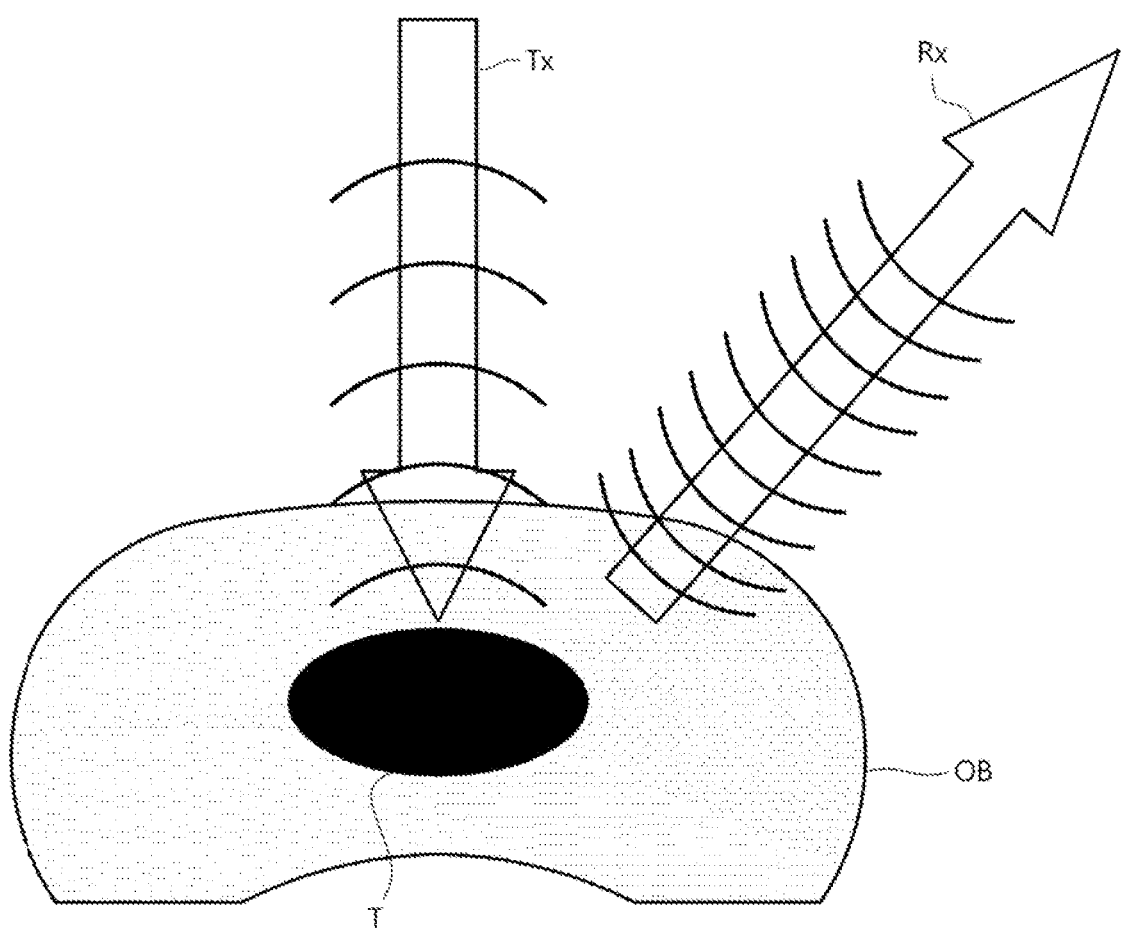
FIG. 6 is a conceptual diagram illustrating ultrasonic waves reflected from a specific part of an object.
Figure 7:
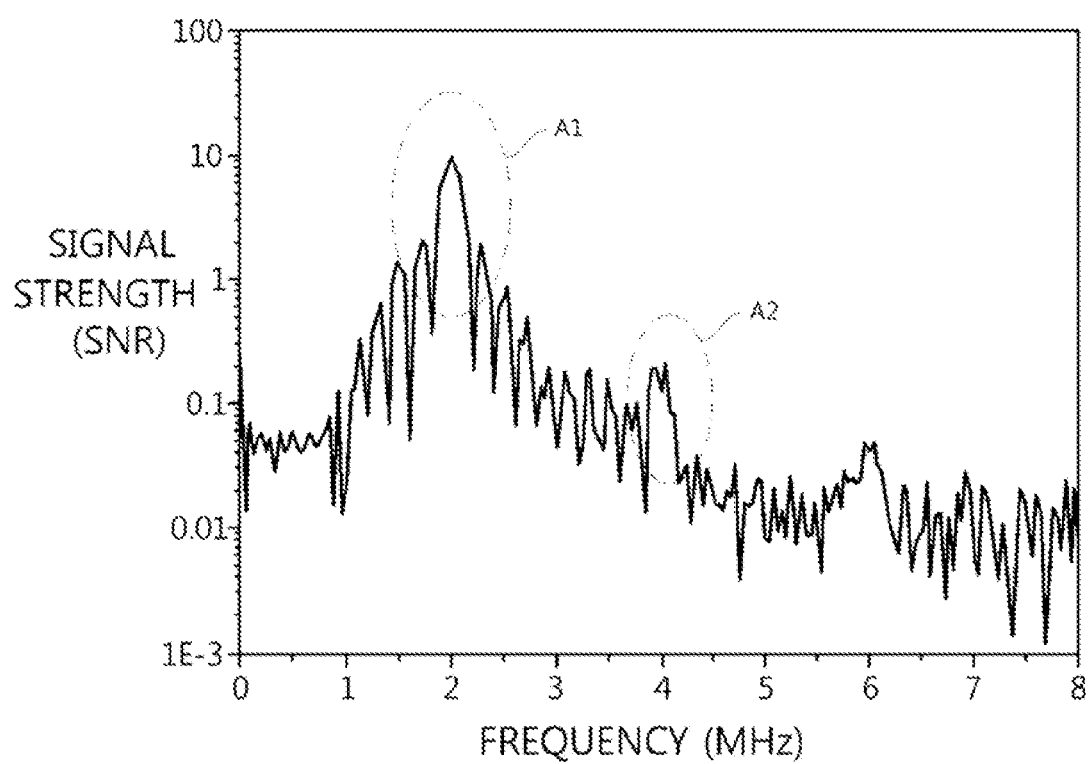
FIG. 7 is a graph illustrating a signal intensity according to a frequency of an input signal (I) corresponding to reflected ultrasonic waves.

FIG. 6 is a conceptual diagram illustrating ultrasonic waves reflected from a specific part of an object. FIG. 7 is a graph illustrating a signal intensity (such as an SNR) depending on a frequency of an input signal (I) corresponding to the reflected ultrasonic waves.

Referring to FIGS. 6 and 7, the incident waves Tx may be distorted while arriving at the target site T of an object OB, e.g., a human body. The intended effect such as thermal deformation may occur at the target site T, and the incident waves Tx are converted into the reflected waves Rx so that the reflected waves Rx may be received by the probe 200.

When the incident waves Tx arrive at the target site T after passing through the object OB, some parts of the incident waves Tx may be absorbed. Thus, about 60 to 80% of the incident waves may be converted into heat at the target site, and the remaining about 20 to 40% of the incident waves may be reflected so that the reflected waves Rx return to the transducers. During the above process, thermal deformation such as, for example, a burned subcutaneous tissue may occur. If the thermal deformation occurs, small air bubbles may be generated, which may be subsequently broken. Due to thermal deformation or destruction of small air bubbles, ultrasonic waves may include many more harmonic components. The amount of harmonic waves may be changed according to the degree of thermal deformation, the degree of generated air bubbles, or the degree of destruction of air bubbles. Generally, if the degree of thermal deformation is high, if a large amount of air bubbles is generated, or if the large amount of air bubbles explode or are destroyed, the incident waves may include increased harmonic components A2, as shown in FIG. 7.

Increased harmonic components A2 may indicate harmonic components having physical significance. For example, although as many harmonic waves as twice, three time, four times or more than four times the frequency of fundamental waves A1 (mathematically, as many harmonic waves as an integer multiple of the fundamental frequency A1 may occur), if harmonic components received by the probe 200 can be segmented or combined, the harmonic components A2 may have a predetermined threshold value or higher.

The harmonic components A2 to be described hereinafter may indicate increased harmonic components A2. In more detail, the harmonic components A2 may be physically isolated, amplified, and/or filtered in a manner that ultrasonic images can be synthesized or combined.

Therefore, each input signal (I) may include a fundamental component A1 and a harmonic component A2.

In addition, the input signal (I) may be modified due to the harmonic components A2 and/or technical or physical characteristics of the probe 200 or the beamformer 350, and noise n may be added to the modified input signal (I). Therefore, the ultrasonic image y generated in response to the input signal (I) may have an unclear edge or much more noise as compared to the raw image x as shown in FIG. 5A. That is, the image quality of the ultrasonic image y is degraded than the raw image x. The relationship between the raw image x and the ultrasonic image y based on noise will hereinafter be described with reference to FIGS. 8A and 8B.

Figure 8A:
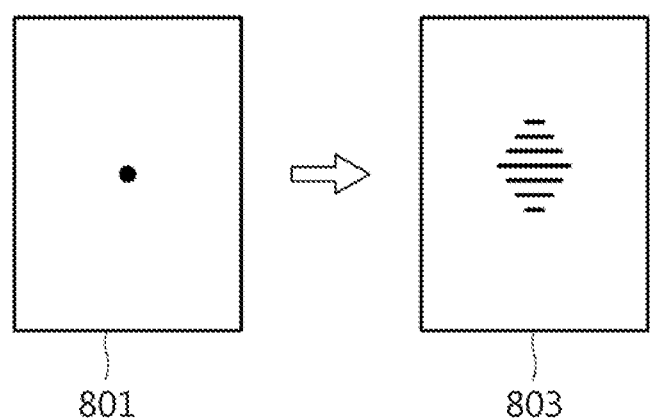
FIGS. 8A and 8B illustrate a contrast between a raw image of a target site inside an object and an ultrasonic image of the target site.

A raw image 801 of the target site, and an ultrasonic image 803 of the target site is shown in FIG. 8A. As can be seen from FIG. 8A, if the raw image 801 of the target site is denoted by a dot, the ultrasound image 803 of the target site is spread in a vertical or horizontal direction. Such difference in image quality between the raw image 801 and the ultrasonic image 803 may gradually increase in proportion to the depth of a target site. In this case, the increasing depth direction of the target site may be defined as an increasing direction of the axis direction of the transducer.

Figure 8B:
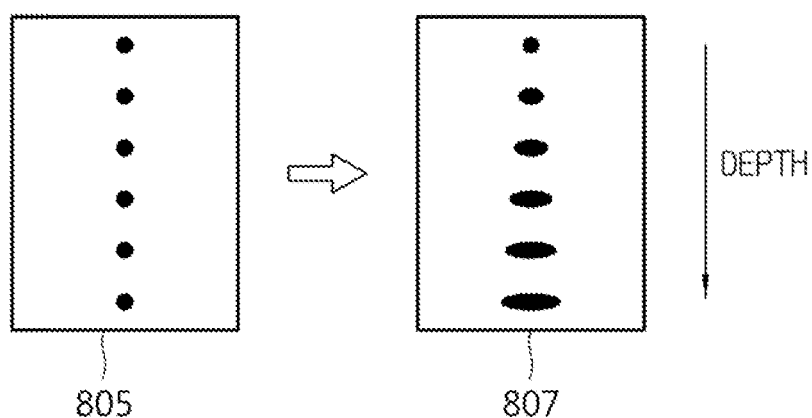

A raw image 805 of the target site, and an ultrasonic image 807 of the target site is shown at the right of FIG. 8B. As can be seen from FIG. 8B, the target site located close to the probe 200 may be displayed in the ultrasonic image 807 in a form similar to the raw image 805 of the target site. However, it can be recognized that the target site located further away from the probe 200 is displayed in the ultrasonic image 807 in a form substantially different from the raw image 80 of the target site.

As described above, the ultrasonic image y having an image quality that is degraded by technical or physical characteristics of the probe 200 and/or the beamformer 350 or noise n may be generated. In this case, if the modification caused by technical or physical characteristics of the probe 200 or the beamformer 350 is denoted by a PSF (h), and noise is denoted by n, the relationship between the raw image x and the ultrasonic image y may be represented by the following equation 1 in a spatial domain.

$$y = x * h + n \qquad \text{[Equation 1]}$$

In Equation 1, x is a raw image, y is an ultrasonic image, h is a point spread function (PSF), n is noise, and * is a convolution.

Assuming that noise is not present, the ultrasonic image y may be represented by a convolution between the raw image x and the PSF (h). Therefore, assuming that it is possible to recognize the PSF (h), the ultrasonic image y and the PSF (h) are deconvoluted to acquire the raw image x corresponding to the ultrasonic image y.

As can be seen from FIG. 5B, the image processor 500 may estimate an appropriate PSF (h), perform deconvolution between the estimated PSF (h) and the ultrasonic image (g), and acquire a reconstructed image R similar to the raw image x of the target site.

In order to acquire a reconstructed image R more similar to the raw image, the image processor 500 may segment an ultrasonic image corresponding to the input signal (I) into a plurality of image sections in a manner that an ultrasonic image corresponding to the input signal (I) is segmented to recognize thermal deformation of the object and/or meaningful harmonic components such as destruction of small air bubbles, and performs deconvolution between each segmented ultrasonic image y and the estimated PSF (h), resulting in a single composite ultrasonic image.

In more detail, the beamformer 350 and the transceiver 505 coupled to the display 720 may receive images from the beamformer 350 through a network, and the image reconstructor 510 may estimate a point spread function (PSF) based on the respective divided ultrasonic images y of individual frequency bands. The image reconstructor 510 may obtain a reconstructed image of the ultrasonic image by performing deconvolution using the estimated PSF. The image post-processor 530 may filter the reconstructed image. The image reconstructor 510 may re-estimate the PSF based on the filtered image, and perform deconvolution. By repeated execution of the above-mentioned process, a more appropriate PSF can be estimated, and the finally obtained reconstructed image becomes identical or similar to a raw image of the target site. Thereafter, the image synthesizer may synthesize reconstructed images of respective ultrasonic images that have been segmented, deconvolution-processed, and filtered.

The image reconstructor 510, the image post-processor 530, and the image synthesizer 550 and the relationship thereamong will hereinafter be described with reference to FIG. 9.

Figure 9:
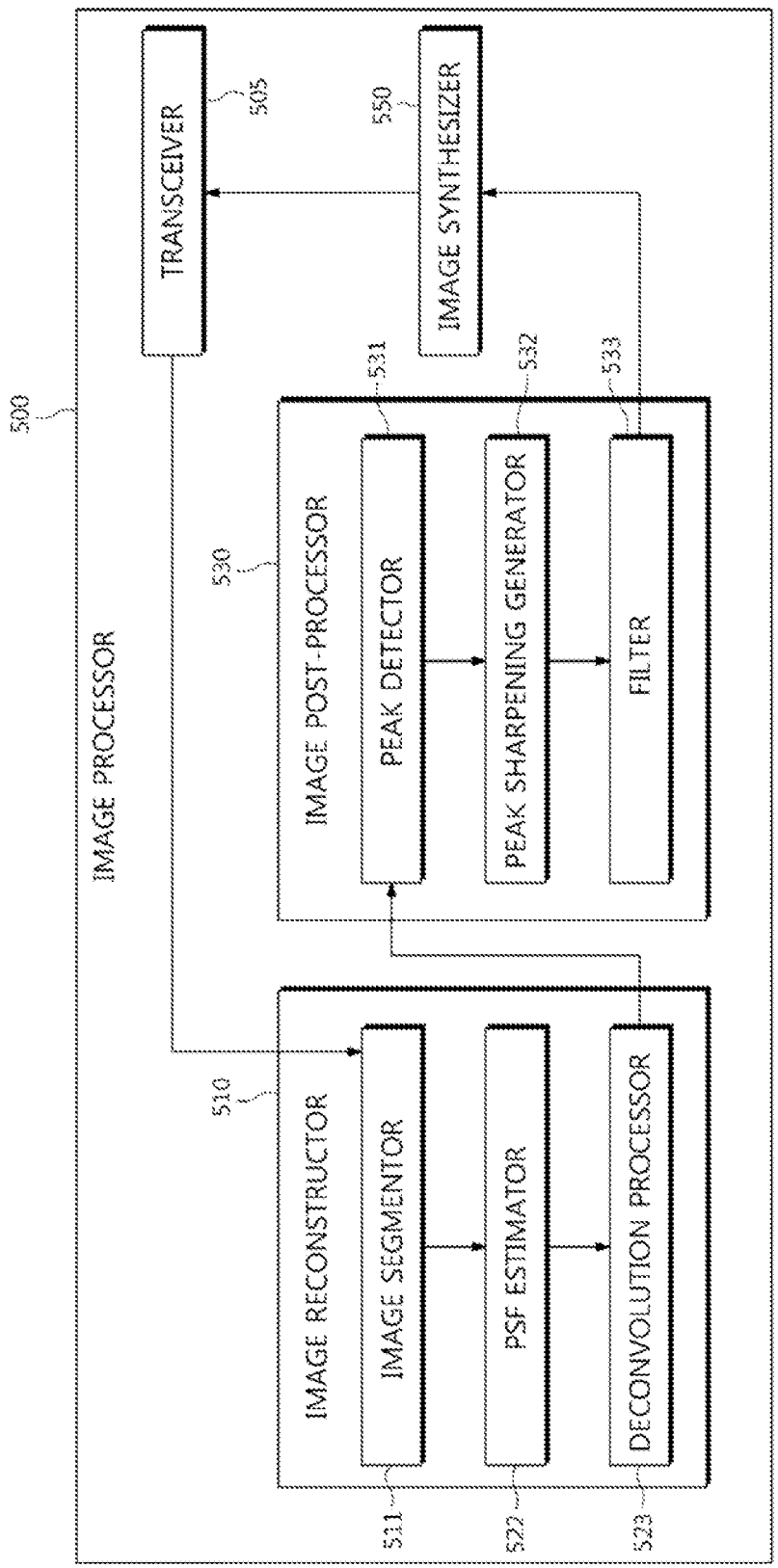
FIG. 9 is a block diagram illustrating an image processor according to an exemplary embodiment.

FIG. 9 is a block diagram illustrating an image processor according to an exemplary embodiment.

Referring to FIGS. 2 and 9, the image reconstructor may include an image segmentor 511, a PSF estimator 522, and a deconvolution processor 523. The image post-processor 530 may include a peak detector 531, a peak sharpening filter generator 532, and a filter 533.

Figure 10:
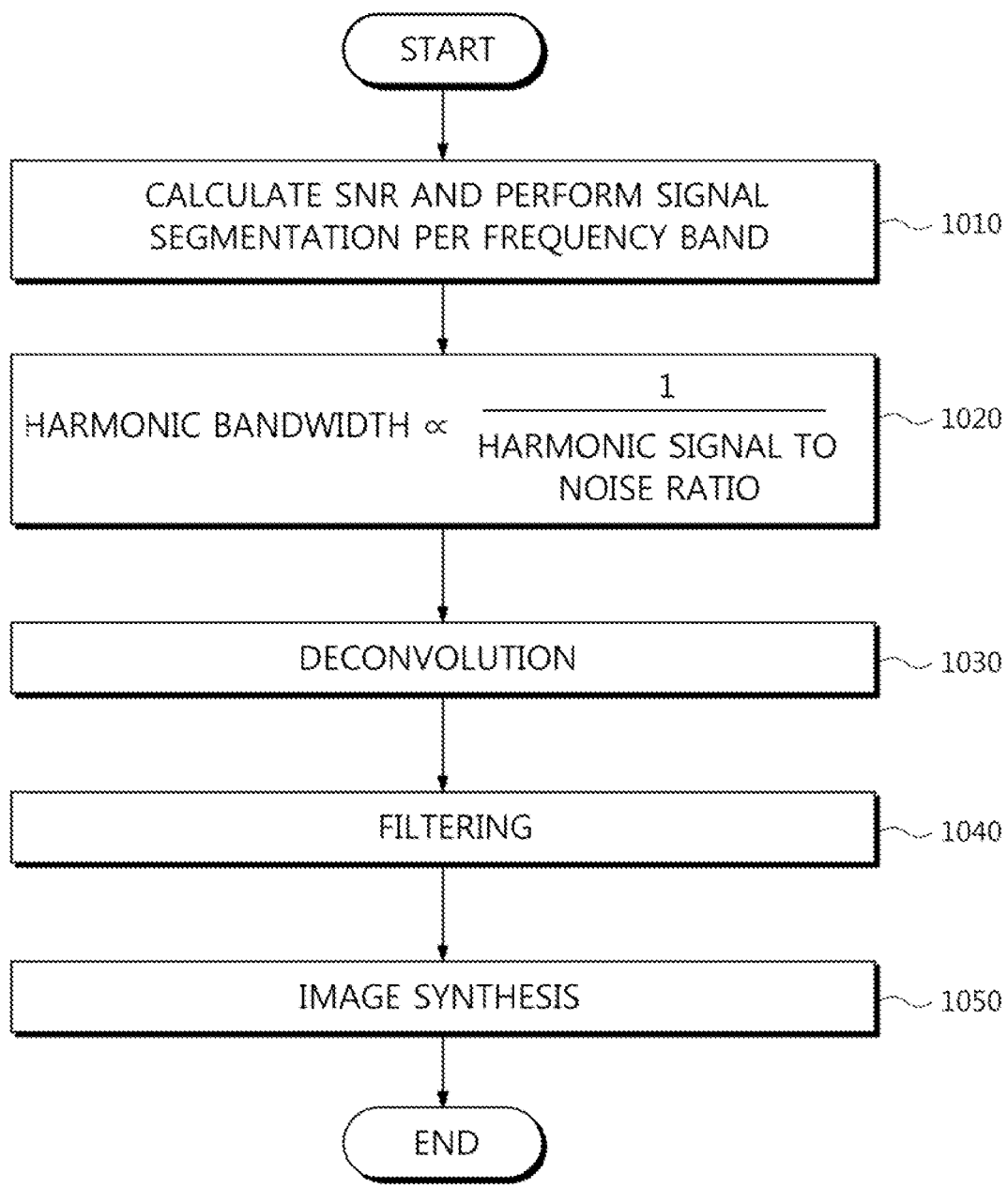
FIG. 10 is a flowchart illustrating a method for segmenting an image received by an image segmentor according to frequency bands or harmonic components.

FIG. 10 is a flowchart illustrating a method for controlling the image reconstructor, the image post-processor, and the image synthesizer.

Referring to FIG. 10, the transceiver 505 of the image processor 500 may receive images from the beamformer 350. The transceiver 505 may be connected to the beamformer 350 or the display 720 over the network, and the network may be implemented as a wired network (for example, a local area network (LAN), a wide area network (WAN) or a value added network (VAN)) or a wireless network such as a satellite communication network. In addition, if the network is implemented in one device along with the beamformer 350 or the display 720, the network may also be integrated or combined with the beamformer 350 or the display 720 within one device. The received image may be transmitted in the form of a signal having various frequencies.

The image segmentor 511 may calculate a signal-to-noise ratio (SNR) in response to a frequency of an ultrasonic image, and may segment an ultrasonic image corresponding to the input signal (I) according to one or more frequency bands in operation 1010. Segmentation of the ultrasonic image may be achieved based on the analysis result of the ultrasonic image. In this case, the presence or absence of a harmonic component may be used as a criterion for performing segmentation.

That is, the image segmentor 511 may segment an ultrasonic image corresponding to the input signal (I) according to respective frequency bands.

Referring again to FIG. 5, the SNR of a frequency region of the ultrasonic image is high in a frequency region located in the vicinity of the fundamental wave component A1 or the harmonic wave component A2 of the ultrasonic image.

Although the ultrasonic image is illustrated as having a fundamental wave component A1 and a secondary harmonic wave component A2, the exemplary embodiments are not limited thereto, the ultrasonic image may further include a harmonic wave, a subharmonic wave, and a fractional wave, each of which has a frequency corresponding to an integer multiple of the fundamental wave component.

Alternatively, the expression "frequency region located in the vicinity of the fundamental wave or the harmonic wave" may indicate a frequency region located in the vicinity of the fundamental or harmonic wave that is arbitrarily sampled by the controller, or may be a region configured by a user or a manufacturer. For convenience of description, the frequency region may be denoted by a frequency domain.

Referring again to FIGS. 9 and 10, the image segmentor 511 of the ultrasonic imaging apparatus may increase a bandwidth of a secondary harmonic frequency domain in inverse proportion to the SNR of the secondary harmonic frequency domain in operation 1020. In more detail, the secondary harmonic frequency domain is extended to the fundamental frequency domain in such a manner that the SNR of the frequency domain of the fundamental wave is equivalent to the SNR of the secondary harmonic frequency domain.

Figure 11A:
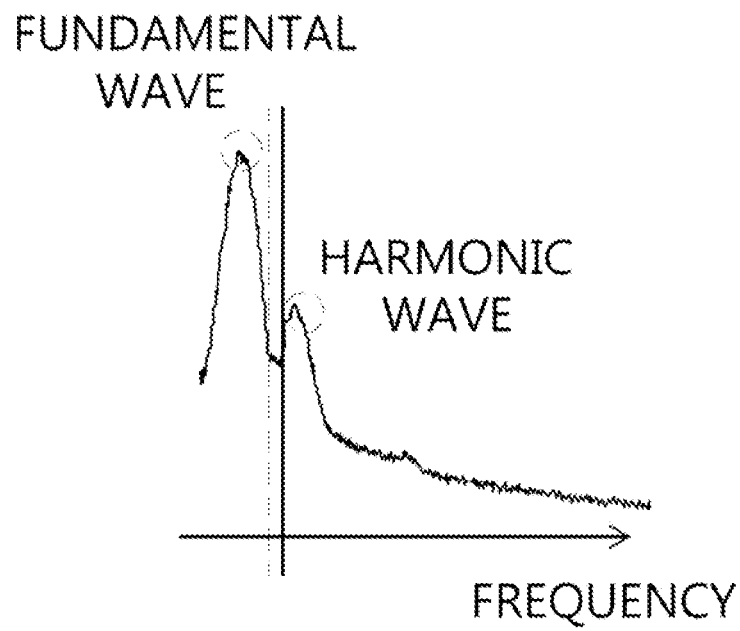
FIGS. 11A, 11B, and 11C are conceptual diagrams illustrating a method for segmenting an ultrasonic image by an image segmentor according to exemplary embodiments.
Figure 11B:
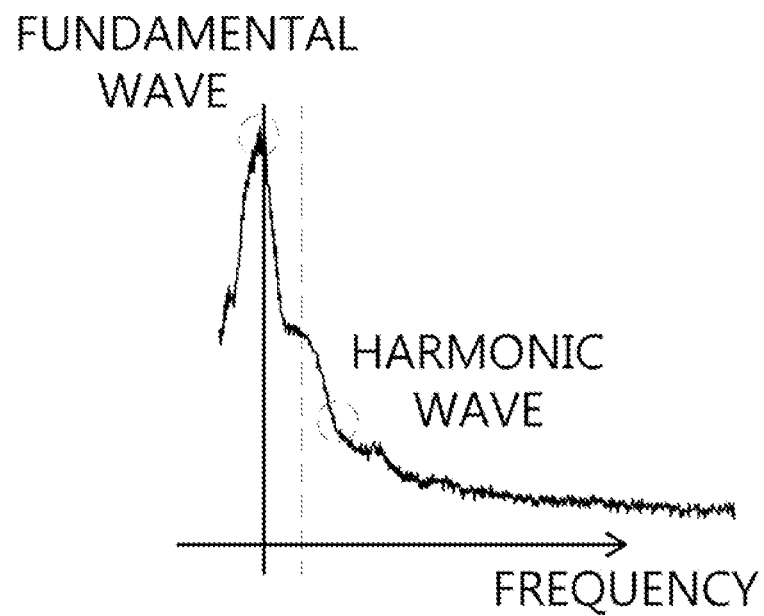
Figure 11C:
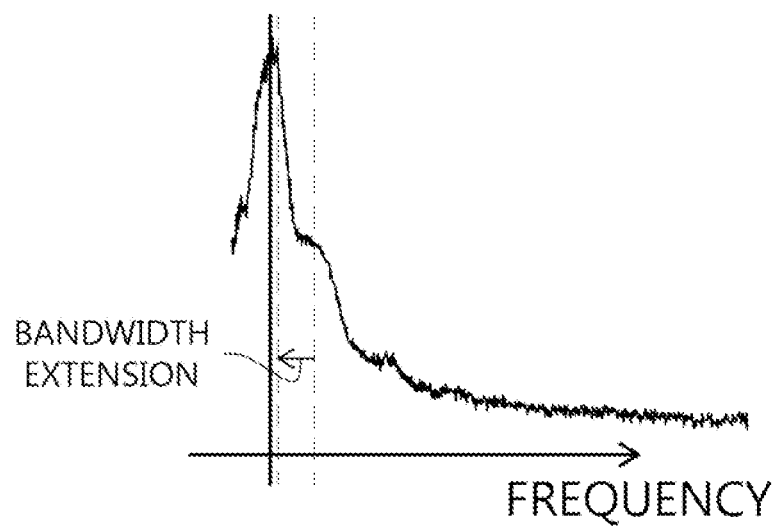

FIGS. 11A, 11B, and 11C are conceptual diagrams illustrating a method for segmenting an ultrasonic image by the image segmentor 511.

Referring to FIG. 11A, the SNR of the secondary harmonic frequency domain of the ultrasonic image is high such that the fundamental frequency domain and the secondary harmonic frequency domain can be definitively distinguished from each other. Therefore, the secondary harmonic frequency domain of FIG. 11A may have a relatively smaller bandwidth as compared to FIG. 11B.

Referring to FIG. 11B, the SNR is very low in the secondary harmonic frequency domain of the ultrasonic image such that it may be difficult to make a distinction between the fundamental frequency band and the secondary harmonic frequency band. In this case, the image segmentor 511 may coordinate a bandwidth of the secondary harmonic frequency domain in a manner that the fundamental frequency domain and the secondary harmonic frequency domain have a substantially uniform SNR. That is, the secondary harmonic frequency domain of FIG. 11B may have a relatively larger bandwidth as compared to FIG. 11A.

Referring to FIG. 11C, the image segmentor 511 may extend the secondary harmonic band to the fundamental frequency domain to increase resolution of the ultrasonic image related to the SNR of FIG. 11B, so that the ultrasonic image can be segmented.

In another exemplary embodiment, the image segmentor 511 may extend the harmonic frequency domain in such a manner that the bandwidth of the harmonic frequency band is larger than the bandwidth of the fundamental band as an object image is located within a short-distance from a focusing-point region (i.e., as the object image is located closer to the focusing-point region). In addition, the image segmentor 511 may reduce the harmonic frequency domain in such a manner that the bandwidth of the harmonic frequency band is smaller than the bandwidth of the fundamental region as an object image is located in a long-distance region from the focusing-point region (or located in a non-focusing-point region). Therefore, speckle noise of ultrasonic images of the short-distance region from the focusing-point region can be suppressed without resolution deterioration, and the SNR of ultrasonic images of the long-distance region from the focusing-point region (or the non-focusing-point region) can be improved.

FIGS. 11A to 11C show an example of a method for segmenting the ultrasonic image for convenience of description, and the exemplary embodiments are not limited thereto. That is, the number of segmentation regions of the ultrasonic image may be higher or less than that of FIGS. 11A to 11C. The image segmentor 511 may segment or divide the ultrasonic image based on other situation variables (e.g., speed of sound, the depth of a target site, etc.) as needed.

If a plurality of ultrasonic images is segmented, the image segmentor 511 may segment each ultrasonic image using the same scheme. For the convenience of description, the detailed operations of the image segmentor 511 will hereinafter be described with respect to a single ultrasonic image shown in FIG. 5 or with respect to a segmented ultrasonic image per frequency band according to the SNR.

Referring to FIGS. 9 and 10, the ultrasonic imaging apparatus performs deconvolution for each ultrasonic image in operation 1030. To accomplish this, the PSF estimator 522 may estimate at least one PSF for an ultrasonic image. In this case, at least one PSF to be estimated may include only one-dimensional PSF or may include two-dimensional PSF. In addition, the one-dimensional PSF and the two-dimensional PSF may also be contained in the at least one PSF. In some exemplary embodiments, at least one PSF may include higher-dimensional PSFs such as a three-dimensional PSF or a four-dimensional PSF.

As one example for estimating the one-dimensional PSF, an autoregressive automoving average (ARMA) scheme may be used. The aforementioned one-dimensional PSF estimation may be performed within a short time.

As one example for estimating the two-dimensional PSF, the Cepstrum scheme may be used. In accordance with the Cepstrum scheme, an ultrasonic image of the spatial domain is converted into a Cepstrum domain, and the two-dimensional PSF is estimated in the Cepstrum domain.

The Cepstrum scheme is classified into a first Cepstrum scheme for estimating the two-dimensional PSF in consideration of the size information of the ultrasonic image and a second Cepstrum scheme for estimating the two-dimensional PSF in consideration of the size and phase information of the ultrasonic image. The estimation method considering only the size information of the ultrasonic image can increase the estimation speed, and the estimation method considering the size information and the phase information can increase the estimation accuracy.

The deconvolution processor 523 performs deconvolution between the PSF estimated by the PSF estimator 522 and each ultrasonic image segmented per frequency band, such that a reconstructed image for each ultrasonic image can be generated. In contrast, although the image reconstructor according to the exemplary embodiments performs deconvolution using the deconvolution processor 523, the exemplary embodiments are not limited thereto, and the image reconstructor may include a demodulator (not shown) for demodulating the modulated ultrasonic image.

As one example of the deconvolution method, the following equation 2 may be used.

$$R = DFT^{-1}\left[\frac{DFT(y)}{DFT(h)}\right] \qquad \text{[Equation 2]}$$

In Equation 2, R is a reconstructed image for each frequency band, y is each segmented ultrasonic image per frequency band, and h is a PSF of Equation 1.

The deconvolution processor 523 may perform deconvolution between the ultrasonic image y and the PSF (h) using equation 2, resulting in a reconstructed image R.

In more detail, if the spread function (h1) is estimated in response to the ultrasonic image of the fundamental frequency band, the deconvolution processor 523 may perform deconvolution between the ultrasonic image of the fundamental frequency band and the spread function (h1) to form a first reconstructed image (R1).

In addition, if the spread function (h2) for an ultrasonic image of the harmonic frequency band is estimated, the deconvolution processor 523 may perform deconvolution between the ultrasonic image of the harmonic frequency band and the spread function (h2) to form a second reconstructed image (R2).

Referring to FIGS. 9 and 10, the ultrasonic imaging apparatus may filter each reconstructed image in operation 1040. For this purpose, the peak detector 531 of the image post-processor 530 may detect a peak point of the reconstructed image of each frequency band received from the deconvolution processor 523.

In this case, the peak point may be a two-dimensional peak point of the two-dimensional image, or may be a one-dimensional peak point of a one-dimensional image corresponding to a cross-sectional view in the lateral direction (L) or the elevation direction (E).

If the peak point is detected by the peak detector 531, the peak sharpening filter generator 532 may generate a peak sharpening filter for emphasizing the peak point of the reconstructed image of each frequency band.

The filter 533 may sequentially filter the respective reconstructed images using the respective peak sharpening filters generated in response to the respective reconstructed images.

The peak detector 531 may detect the peak point, the peak sharpening filter 531 may generate the filter, and the filter 533 performs filtering. A detailed description thereof will be given with reference to FIGS. 12 and 13.

Figure 12A:
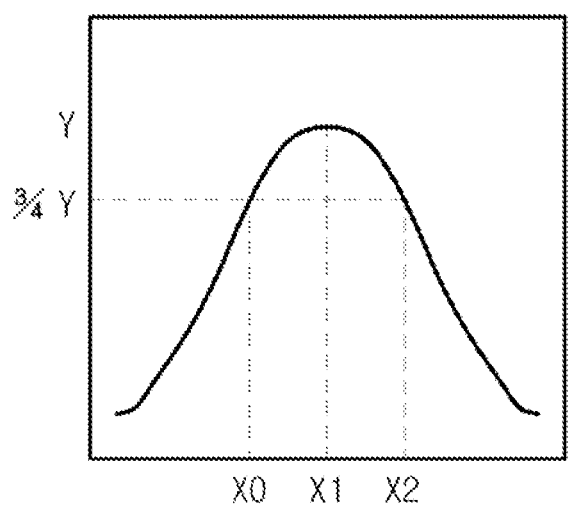
FIGS. 12A, 12B, and 12C are conceptual diagrams illustrating a method for generating a peak sharpening filter according to an exemplary embodiment.
Figure 12B:
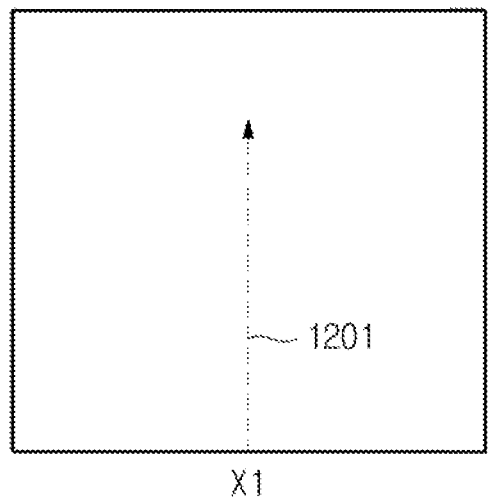
Figure 12C:
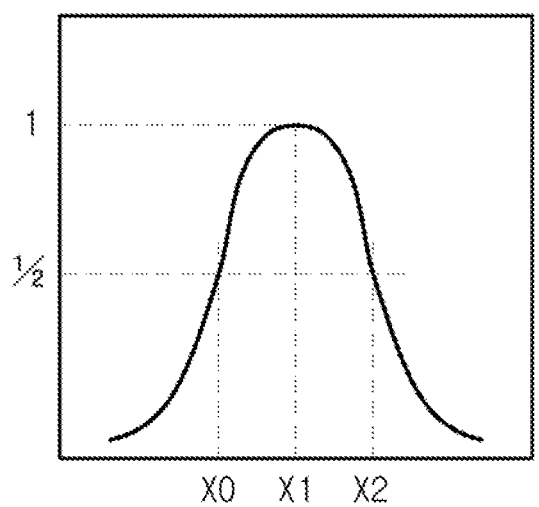

FIGS. 12A, 12B, and 12C are conceptual diagrams illustrating a method for generating a peak sharpening filter.

In more detail, FIG. 12A exemplarily shows coordinates of the image and image values, FIG. 12B exemplarily shows the peak point of the image, and FIG. 12C exemplarily shows the peak sharpening filter (F1) generated based on the peak point. In this case, the image may be a reconstructed image formed by deconvolution. In FIGS. 12A to 12C, the horizontal axis may denote coordinates of the spatial region, the vertical axis of FIG. 12A may denote image values, and the vertical axis of FIG. 12C may denote a filter value.

As can be seen from FIG. 12A, an image value of the coordinate X1 of the image is denoted by Y. The image value is gradually reduced in proportion to a distance from the coordinate X1, so that the image value of the coordinate X0 or X2 is denoted by ¾Y. If a specific point having a higher image value than a peripheral region is set to a peak point, the peak detector 531 may detect X1 as a peak point as shown in FIG. 12B, resulting in creation of an impulse signal 1201.

If the impulse signal 1201 for the peak point X1 is formed as described above, the peak sharpening filter generator 532 may apply a low pass filter (LPF) to the impulse signal 1201, resulting in creation of a Gaussian form. That is, it may be possible to generate a filter, a filter value of which is gradually reduced in proportion to a distance from the peak point. Accordingly, the peak sharpening filter generator 532 may generate a filter as shown in FIG. 12C. In case of using this filter shown in FIG. 12C, a filter value of the peak point X1 is set to 1, and the filter value of the coordinate X0 or X2 spaced apart from the peak point is set to ½.

As described above, if the peak sharpening filter generator 532 generates the Gaussian-shaped peak sharpening filter as described above, the filter 533 may perform filtering to obtain an inner product between a reconstructed image obtained by deconvolution and the peak sharpening filter generated in response to the reconstructed image. Therefore, a peak point of the reconstructed image can be emphasized, i.e., the peak point of the reconstructed image may be sharpened.

Figure 13:
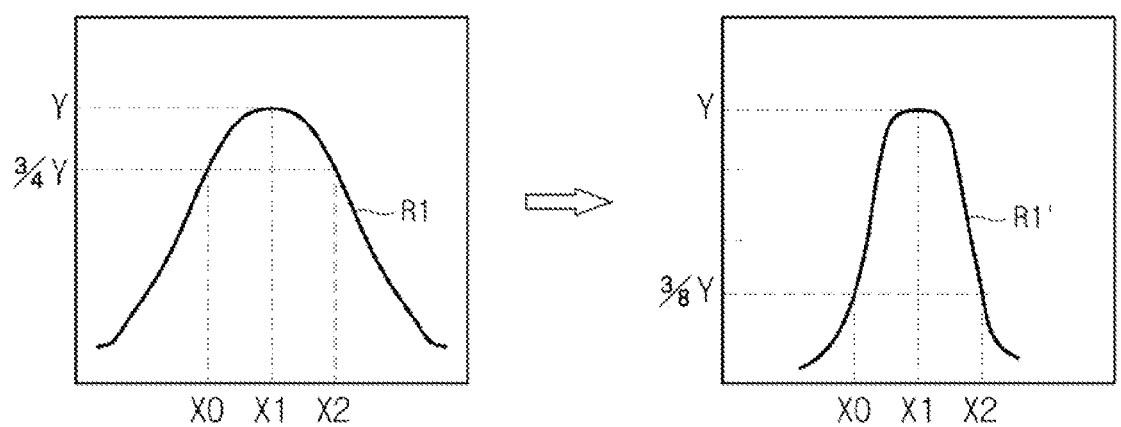
FIG. 13 illustrates comparison between image values of an image obtained before filtering and an image obtained after filtering.

FIG. 13 illustrates comparison between image values of an image obtained before filtering and an image obtained after filtering. In FIG. 13, a graph R1 corresponds to an image as shown in FIG. 12 A obtained before filtering, and a graph R1' corresponds to an image obtained after filtering as shown in FIG. 12C.

In the image obtained after filtering, the peak point X1 has an image value Y in the same manner as in the image obtained before filtering. However, the degree of reduction of an image value according to the distance from the peak point X1 is higher in the graph R1' (i.e., after filtering) than in the graph R1 (i.e., before filtering). For example, the coordinate X0 or X2 having an image value of ¾Y in the graph R1 is converted into the image value of ⅜Y in the graph R1'.

That is, the peak point of the image after filtering is sharpened than the image before filtering.

As described above, the filter 533 may filter a reconstructed image corresponding to each frequency band received from the deconvolution processor 523.

The image post-processor 530 may perform, as the post-processing stage of the reconstructed image, a noise reduction (NR) process for reducing noise increased by convolution. As examples of the noise reduction (NR) method, wavelet shrinkage in a wavelet region, a median filter, a bilateral filter, etc. may be used, and log compression and a digital scan converter (DSC) may also be used as needed.

Referring again to FIGS. 9 and 10, the ultrasonic imaging apparatus may synthesize images to combine respective reconstructed images in operation 1050. To accomplish this, the image synthesizer 550 may combine reconstructed images of the respective filtered frequency bands into one image, and may amplify the signal strength of a specific frequency band so that the image synthesizer 550 may synthesize the images. For this purpose, the image synthesizer 550 may include an image combiner 551, a binary image generator 552, a contrast-to-noise ratio (CNR) calculator 553, and a weight applier 554.

The image combiner 551 may combine reconstructed images of the respective frequency bands received from the filter 533 to form a first combined image. The first combined image may be transferred to the display 720 through the transceiver 505.

Figure 14A:
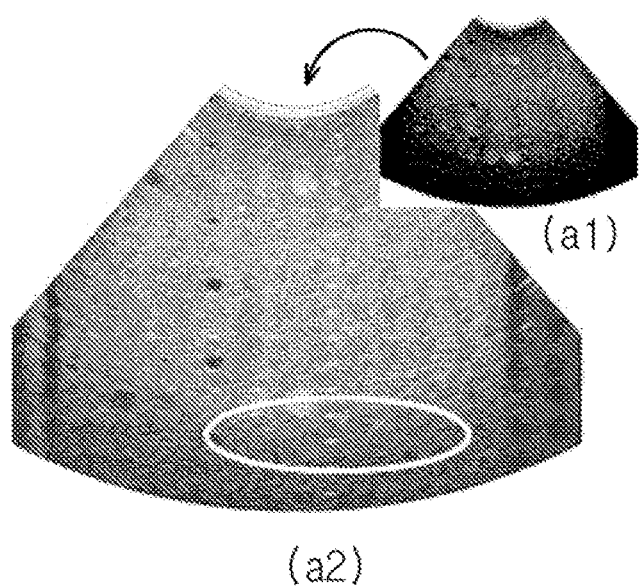
FIGS. 14A and 14B illustrate a contrast between an ultrasonic image corresponding to an input signal (I) and a first combined image generated by an image combiner.
Figure 14B:
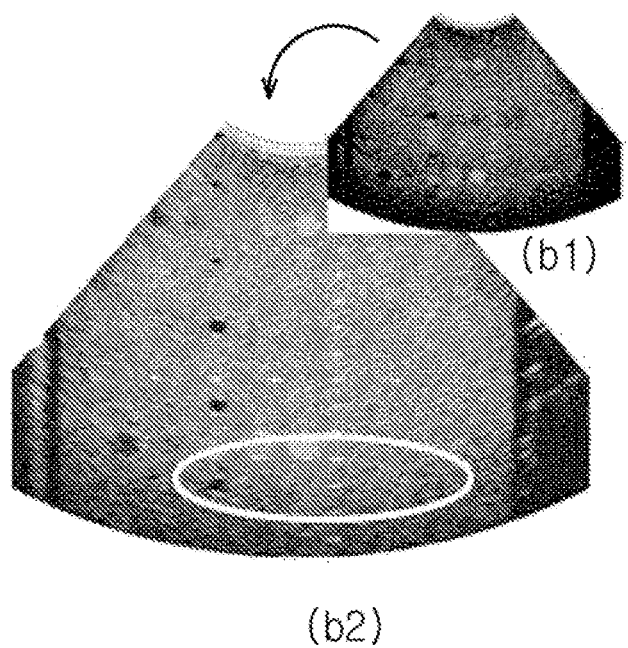

FIGS. 14A and 14B illustrate a contrast between ultrasonic images (a1), (a2) corresponding to an input signal (I) and first combined images (b1), (b2) generated by the image combiner 551. The images (a2) and (b2) are enlarged images of the images (a1) and (b2), respectively.

Referring to FIG. 14, it is shown that the first combined image (b2) to which image segmentation and deconvolution of the image reconstructor are applied has a more uniform brightness and a lower number of speckles than the ultrasonic image (a2). That is, the image resolution can be improved in the first combined image (b2), resulting in reduction of noise.

In accordance with another exemplary embodiment, the image processor 500 can adaptively synthesize the respective recovery images using the contrast-to-noise ratio (CNR) of the reconstructed image, and can also form a second combined image.

Figure 15:
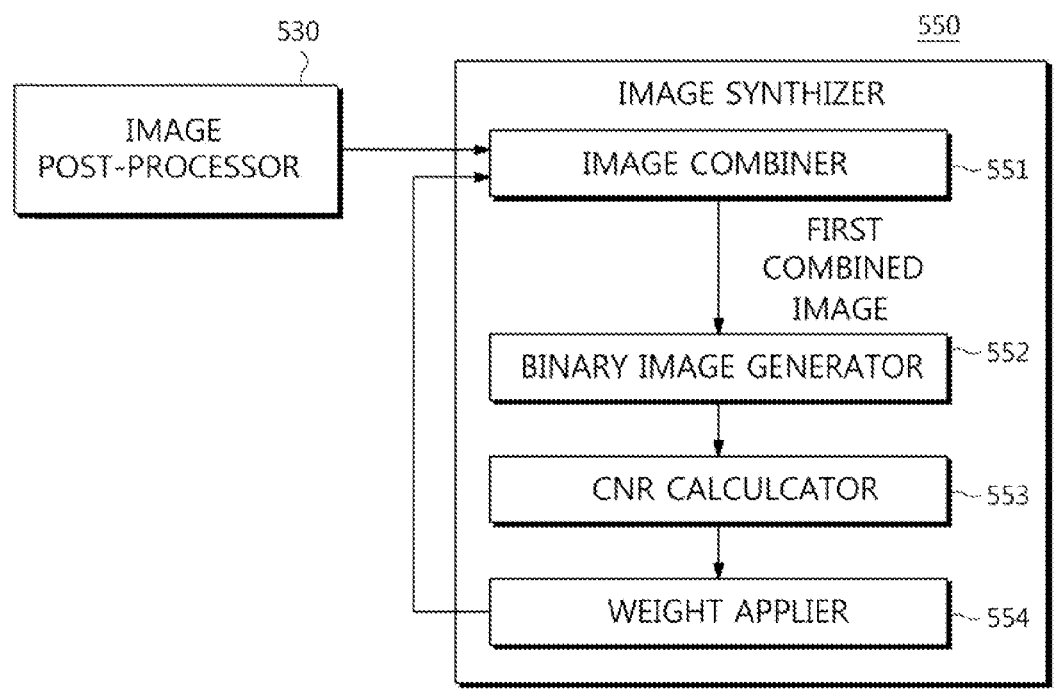
FIG. 15 is a block diagram illustrating an image synthesizer according to an exemplary embodiment.

FIG. 15 is a block diagram illustrating an image synthesizer according to an exemplary embodiment. Referring to FIG. 15, the image synthesizer 550 may further include an image combiner 551 to form a combined image by combining the respective reconstructed images, a binary image generator 552 to perform binary coding of the first combined image, a CNR calculator 553 to calculate a CNR of a region of interest (or desired region), and a weight applier 554 to perform image synthesis by applying a weight to the respective reconstructed images.

The binary image generator 552 may perform thresholding of the first combined image formed by the image combiner 551 based on a predetermined threshold value, and may classify pixel regions of the first combined image into a dark region and a bright region. In contrast, the binary image generator 552 may also perform thresholding of the first combined image and an ultrasonic image corresponding to the input signal (I) based on a predetermined threshold value.

The predetermined threshold value may be predetermined by the user, and may be entered by the user who uses an input unit while in use. However, the predetermined threshold value may be predetermined in the manufacturing stage.

Subsequently, the CNR calculator 553 may calculate a contrast-to-noise ratio (CNR) of a random interest region from among the bright region or the dark region. The CNR may indicate the magnitude of a ratio of contrast to noise, and may also indicate a contrast resolution so that it indicates a relative signal strength of a background in the corresponding region.

In this case, the CNR calculator 553 may calculate the CNR as represented by the equation 3.

$$CNR = \left| \frac{(\text{Background } SI_{Avg} - ROI\ SI_{Avg})}{\sqrt{\text{Background } SD^2 + ROI\ SD^2}} \right| \quad \text{[Equation 3]}$$

In Equation 3, ROI is a region of interest (i.e., a target region to be observed), Background is a region that is not of interest, $SI_{Avg}$ is an average of the signal magnitudes, SD is a standard deviation (SD).

Subsequently, the weight applier 554 may allocate a weight calculated by a weight calculator (not shown) configured to calculate a weight of harmonic components for each region according to the CNR value, to the respective regions.

For example, if the CNR calculator 553 calculates the CNR of the first region of interest as 10 dB, and calculates the CNR of the second region of interest as 20 dB, the weight applier 554 may allocate a higher weight to a reconstructed image of the harmonic frequency band of the second region of interest as compared to the reconstructed image of the harmonic frequency band of the first region of interest, as represented by the following equation 4.

$$R = w * rf + (1 - w) * rh \quad \text{[Equation 4]}$$
$$w = f(\min(rc, th)),\ rc = \left(\frac{rf + rh}{2}\right)$$

In Equation 4, R is the resultant image of the weight applier, rf is a reconstructed image of the fundamental frequency band, rh is a reconstructed image of the harmonic frequency band, w is a weight, f is a calculation method of the weight calculator, and th is a threshold value.

That is, the weight applier 554 may compare an average value and a threshold value of the reconstructed image signal strength of the fundamental frequency band with those of the reconstructed image signal strength of the harmonic frequency band. If the average value is less than the threshold value, the weight applier 554 determines the corresponding region to be a dark region, and assigns a first weight to a harmonic component (e.g., a reconstructed image of the secondary harmonic frequency band) of the region of interest according to the CNR. If the average value is higher than the threshold value, the weight applier 554 determines the corresponding region to be a bright region, and may assign a second weight to the bright region. In Equation 4, the first weight may be set to any of 0 to 1, and the second weight may be set to 0.5 to assign a uniform weight to the fundamental wave and the harmonic wave.

In addition, the first weight of the harmonic component (e.g., a reconstructed image of the secondary harmonic frequency band) of the region of interest allocated in response to the CNR may be proportional to the CNR.

Subsequently, the image combiner 551 may combine pixel regions to which weights of the harmonic components (e.g., reconstructed images of the secondary harmonic frequency band) are allocated, resulting in formation of the secondary combined image. The second combined image may be transferred to the display 720 through the transceiver 505.

Figure 16A:
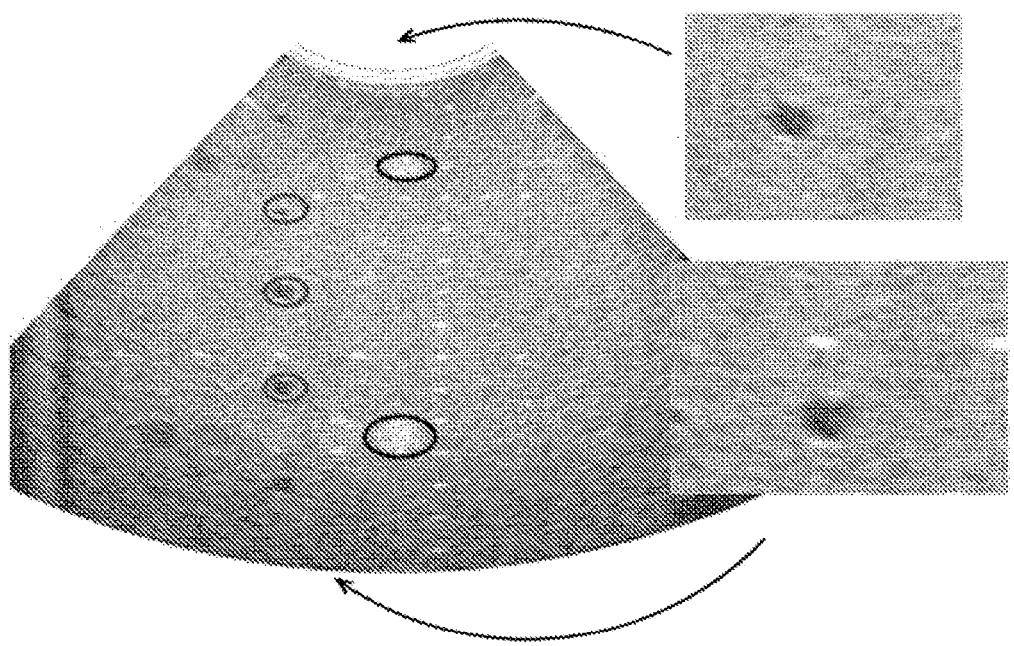
FIG. 16A illustrates the contrast between an ultrasonic image corresponding to an input signal (I) and FIG. 16B illustrates a second combined image generated by an image combiner.
Figure 16B:
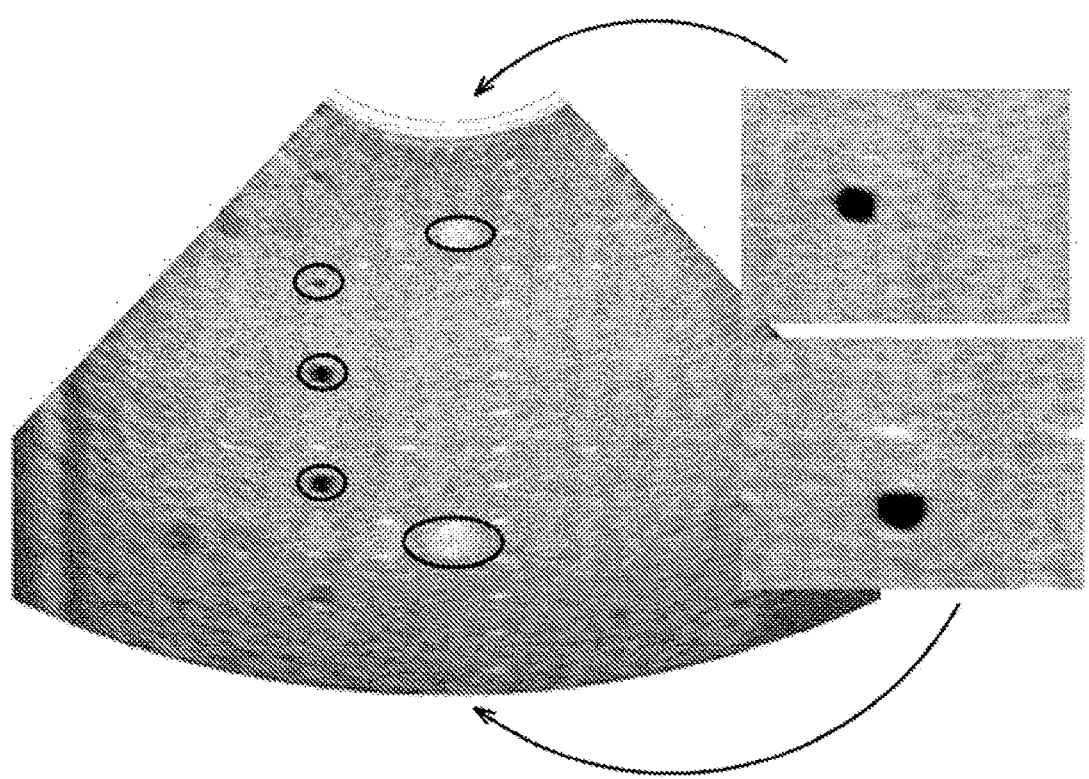

FIG. 16A illustrates the contrast between an ultrasonic image corresponding to an input signal (I) and FIG. 16B illustrates a second combined image generated by an image combiner according to an exemplary embodiment.

Referring to FIGS. 16A and 16B, the CNR of the dark region can be improved by image segmentation of the image reconstructor and image synthesis of the image synthesizer, and the combined image having reduced clutter noise can be formed.

As is apparent from the above description, the image processing apparatus and the method for controlling the same according to the exemplary embodiments can adaptively perform image segmentation such that image noise is suppressed, resulting in improvement of signal-to-noise ratio (SNR).

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An apparatus for processing a medical image, the apparatus comprising:
   a receiver configured to receive a signal having a plurality of frequency bands;
   an image processor configured to segment the signal into a first signal of a first frequency band and a second signal of a second frequency band based on a signal strength, configured to generate a first reconstructed image of the first frequency band and a second reconstructed image of the second frequency band, and configured to synthesize the first reconstructed image and the second reconstructed image,
   wherein the image processor is configured to apply different weights to the first reconstructed image and the second reconstructed image according to a contrast-to-noise ratio (CNR) of a region of interest, and configured to synthesize the first reconstructed image and the second reconstructed image to which the different weights are applied.

2. The apparatus according to claim 1, wherein the image processor is configured to segment the signal such that the first signal of the first frequency band and the second signal of the second frequency band have a substantially uniform signal strength.

3. The apparatus according to claim 1, wherein:
   the image processor is configured to segment the signal into the first signal of a fundamental band and the second signal of a harmonic band, the first signal of the harmonic band signal having a signal-to-noise ratio (SNR) being equal to or greater than a threshold value; and
   is configured to generate a reconstructed image of the fundamental band and a reconstructed image of the harmonic band.

4. The apparatus according to claim 3, wherein the image processor is configured to gradually extend a bandwidth of the harmonic band in response to the signal from an area that is located closer to a region of a focusing point.

5. The apparatus according to claim 1, wherein the image processor is configured to perform deconvolution on the first and second signals.

6. The apparatus according to claim 1, wherein the image processor is configured to generate the first or second reconstructed image by estimating a point spread function (PSF) of the first or second signal, and performing deconvolution on the estimated point spread function (PSF) and the corresponding first or second signal.

7. The apparatus according to claim 1, wherein the image processor comprises:
   an image segmentor configured to segment the signal into the first signal of the first frequency band and the signal of the second frequency band;
   a point spread function (PSF) estimator configured to estimate a point spread function (PSF) of the first or second signal; and
   a deconvolution processor configured to generate the first reconstructed image or the second reconstructed image by performing deconvolution on the estimated point spread function (PSF) and the corresponding first or second signal.

8. The apparatus according to claim 1, wherein the image processor is configured to apply a weight proportional to a contrast strength of a region of interest to the second reconstructed image, and is configured to synthesize the second reconstructed image, to which the weight is applied, and the first reconstructed image.

9. The apparatus according to claim 1, wherein the image processor is configured to generate a combined image by synthesizing the first reconstructed image and the second reconstructed image, and configured to divide the combined image into first and second regions through binary coding of the combined image,
   wherein, in the first region, different weights are applied to the first reconstructed image and the second reconstructed image according to a contrast-to-noise ratio (CNR) strength of a region of interest, and
   in the second region, the same weight is applied to the first reconstructed image and the second reconstructed image.

10. The apparatus according to claim 1, wherein the image processor includes:
    an image combiner configured to generate a combined image by combining the first reconstructed image and the second reconstructed image;
    a binary image generator configured to perform binary coding on the combined image according to brightness;
    a contrast-to-noise ratio (CNR) calculator configured to calculate a CNR of a region of interest; and
    a weight applier configured to apply different weights to the first reconstructed image and the second reconstructed image according to the CNR of the region of interest.

11. The apparatus according to claim 10, wherein the image combiner is configured combine the first reconstructed image and the second reconstructed image to which different weights are applied.

12. The apparatus according to claim 1, wherein the image processor is configured to extend a bandwidth of the second frequency band to the first frequency band.

13. The apparatus according to claim 1, wherein the image processor is configured to perform demodulation on the first signal and perform deconvolution on the second signal.

14. A method for processing a medical image, the method comprising:
    receiving a signal having a plurality of frequency bands;

segmenting the signal into a first signal of a first frequency band and a second signal of a second frequency band based on a signal strength;

generating a first reconstructed image of the first frequency band and a second reconstructed image of the second frequency band; and synthesizing the first reconstructed image and the second reconstructed image, wherein the synthesizing comprises applying different weights to the first reconstructed image and the second reconstructed image according to a contrast strength of a region of interest and synthesizing the first reconstructed image and the second reconstructed image to which the different weights are applied.

15. The method according to claim 14, wherein the segmenting comprises:

segmenting the signal such that the first signal of the first frequency band and the second signal of the second frequency band have a substantially uniform signal strength.

16. The method according to claim 14, wherein:

the segmenting comprises segmenting the signal into the first signal of a fundamental frequency band and the second signal of a harmonic frequency band, the first signal of the harmonic frequency band signal having a signal-to-noise ratio (SNR) being equal to or greater than a threshold value; and the generating comprises generating a reconstructed image of the fundamental frequency band and a reconstructed image of the harmonic frequency band.

17. The method according to claim 16, wherein the segmenting comprises gradually extending a bandwidth of the harmonic band in response to the signal from an area that is located closer to a region of a focusing point.

18. The method according to claim 14, wherein the generating comprises performing deconvolution on the first and second signals.

19. The method according to claim 14, wherein the synthesizing comprises applying a weight proportional to a contrast strength of a region of interest to the second reconstructed image and synthesizing the second reconstructed image, to which the weight is applied, and the first reconstructed image.

20. The method according to claim 14, wherein the synthesizing comprises:

generating a combined image by synthesizing the first reconstructed image and the second reconstructed image; and dividing the combined image into first and second regions through binary coding of the combined image, wherein, in the first region, the same weight is applied to the first reconstructed image and the second reconstructed image, and in the second region, different weights are applied to the first reconstructed image and the second reconstructed image according to a contrast strength of the region of interest.

21. The method according to claim 14, wherein the segmenting comprises extending a bandwidth of the second frequency band to the first frequency band.

22. The method according to claim 14, wherein the generating comprises performing demodulation on the first signal and performing deconvolution on the second signal.

* * * * *